(12) United States Patent
Vase et al.

(10) Patent No.: US 8,340,772 B2
(45) Date of Patent: Dec. 25, 2012

(54) BROWN ADIPOSE TISSUE UTILIZATION THROUGH NEUROMODULATION

(75) Inventors: Abhi Vase, Mountain View, CA (US); Johann Neisz, Coon Rapids, MN (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 259 days.

(21) Appl. No.: 12/774,073

(22) Filed: May 5, 2010

(65) Prior Publication Data

US 2010/0312295 A1 Dec. 9, 2010

Related U.S. Application Data

(60) Provisional application No. 61/176,829, filed on May 8, 2009.

(51) Int. Cl.
*A61N 1/34* (2006.01)

(52) U.S. Cl. ............................................ 607/46; 607/40

(58) Field of Classification Search ................... 607/2, 9, 607/40, 46
See application file for complete search history.

(56) References Cited

U.S. PATENT DOCUMENTS

| | | | |
|---|---|---|---|
| 3,911,930 A | 10/1975 | Hagfors et al. | |
| 4,315,509 A | 2/1982 | Smit | |
| 4,501,264 A | 2/1985 | Rockey | |
| 4,549,556 A | 10/1985 | Tarjan et al. | |
| 4,573,481 A | 3/1986 | Bullara | |
| 4,592,339 A | 6/1986 | Kuzmak et al. | |
| 4,595,010 A | 6/1986 | Radke | |
| 4,702,254 A | 10/1987 | Zabara | |
| 4,827,935 A | 5/1989 | Geddes et al. | |
| 4,867,164 A | 9/1989 | Zabara | |
| 5,095,905 A | 3/1992 | Klepinski | |
| 5,107,833 A | 4/1992 | Barsness | |
| 5,121,754 A | 6/1992 | Mullett | |
| 5,154,172 A | 10/1992 | Terry, Jr. et al. | |
| 5,179,950 A | 1/1993 | Stanislaw | |
| 5,186,170 A | 2/1993 | Varrichio et al. | |
| 5,188,104 A | 2/1993 | Wernicke et al. | |
| 5,205,285 A | 4/1993 | Baker, Jr. | |
| 5,215,086 A | 6/1993 | Terry, Jr. et al. | |
| 5,215,089 A | 6/1993 | Baker, Jr. | |
| 5,222,494 A | 6/1993 | Baker, Jr. | |

(Continued)

FOREIGN PATENT DOCUMENTS

JP 06165827 6/1994

(Continued)

OTHER PUBLICATIONS

Accornero, Neri, et al., "Selective Activation of Peripheral Nerve Fibre Groups of Different Diameter by Triangular Shaped Stimulus Pulses," J. Physiol. 273: 539-560, 1977.

(Continued)

*Primary Examiner* — Rex R Holmes
(74) *Attorney, Agent, or Firm* — Craig Hoersten; Christopher S. L. Crawford

(57) ABSTRACT

Methods and devices for improved neurostimulation to treat obesity. Some methods include measuring temperature increases in Brown Adipose Tissue (BAT) during intraoperative test stimulations to determine the proper nerve electrode placement for implantation. Methods can include determining the side of the patient having the most BAT, and stimulating preferentially on that right or left side. The BAT maybe used to burn fat by stimulating the sympathetic nervous system innervating the BAT deposits.

9 Claims, 18 Drawing Sheets

U.S. PATENT DOCUMENTS

| | | | |
|---|---|---|---|
| 5,231,988 A | 8/1993 | Wernicke et al. |
| 5,235,980 A | 8/1993 | Varrichio et al. |
| 5,237,991 A | 8/1993 | Baker, Jr. et al. |
| 5,251,634 A | 10/1993 | Weinberg |
| 5,263,480 A | 11/1993 | Wernicke et al. |
| 5,269,303 A | 12/1993 | Wernicke et al. |
| 5,281,581 A | 1/1994 | Cooper et al. |
| 5,299,569 A | 4/1994 | Wernicke et al. |
| 5,304,206 A | 4/1994 | Baker, Jr. et al. |
| 5,306,300 A | 4/1994 | Berry |
| 5,330,507 A | 7/1994 | Schwartz |
| 5,330,515 A | 7/1994 | Rutecki et al. |
| 5,335,657 A | 8/1994 | Terry, Jr. et al. |
| 5,351,394 A | 10/1994 | Weinberg |
| 5,423,872 A | 6/1995 | Cigaina |
| 5,454,840 A | 10/1995 | Krakovsky et al. |
| 5,458,626 A | 10/1995 | Krause |
| 5,515,848 A | 5/1996 | Corbett, III et al. |
| 5,531,778 A | 7/1996 | Maschino et al. |
| 5,540,730 A | 7/1996 | Terry, Jr. et al. |
| 5,540,734 A | 7/1996 | Zabara |
| 5,571,150 A | 11/1996 | Wernicke et al. |
| 5,690,691 A | 11/1997 | Chen et al. |
| 5,707,400 A | 1/1998 | Terry, Jr. et al. |
| 5,716,392 A | 2/1998 | Bourgeois et al. |
| 5,725,563 A | 3/1998 | Klotz |
| 5,755,750 A | 5/1998 | Petruska et al. |
| 5,782,798 A | 7/1998 | Rise |
| 5,820,584 A | 10/1998 | Crabb |
| 5,836,994 A | 11/1998 | Bourgeois |
| 5,861,014 A | 1/1999 | Familoni |
| 5,866,547 A | 2/1999 | Flier et al. |
| 5,868,141 A | 2/1999 | Ellias |
| 5,919,216 A | 7/1999 | Houben et al. |
| 5,922,015 A | 7/1999 | Schaldach |
| 5,928,272 A | 7/1999 | Adkins et al. |
| 5,995,872 A | 11/1999 | Bourgeois |
| 6,026,326 A | 2/2000 | Bardy |
| 6,041,258 A | 3/2000 | Cigaina |
| 6,058,331 A | 5/2000 | King |
| 6,068,596 A | 5/2000 | Weth et al. |
| 6,097,984 A | 8/2000 | Douglas |
| 6,109,269 A | 8/2000 | Rise et al. |
| 6,129,685 A | 10/2000 | Howard, III |
| 6,146,391 A | 11/2000 | Cigaina |
| 6,146,416 A | 11/2000 | Andersen et al. |
| 6,165,180 A | 12/2000 | Cigaina |
| 6,169,924 B1 | 1/2001 | Meloy et al. |
| 6,243,607 B1 | 6/2001 | Mintchev et al. |
| 6,308,105 B1 | 10/2001 | Duysens et al. |
| 6,321,124 B1 | 11/2001 | Cigaina |
| 6,350,455 B1 | 2/2002 | Donovan |
| 6,356,786 B1 | 3/2002 | Rezai et al. |
| 6,356,787 B1 | 3/2002 | Rezai et al. |
| 6,381,495 B1 | 4/2002 | Jenkins |
| 6,438,423 B1 | 8/2002 | Rezai et al. |
| 6,497,718 B1 | 12/2002 | Dewan |
| 6,535,764 B2 | 3/2003 | Imran et al. |
| 6,542,776 B1 | 4/2003 | Gordon et al. |
| 6,558,320 B1 | 5/2003 | Causey et al. |
| 6,572,627 B2 | 6/2003 | Gabbay |
| 6,587,719 B1 | 7/2003 | Barrett et al. |
| 6,600,954 B2 | 7/2003 | Cohen et al. |
| 6,645,229 B2 | 11/2003 | Matsumura et al. |
| 6,675,809 B2 | 1/2004 | Stack et al. |
| 6,721,603 B2 | 4/2004 | Zabara et al. |
| 6,758,219 B2 | 7/2004 | Sapala et al. |
| 6,879,859 B1 | 4/2005 | Boveja |
| 6,885,888 B2 | 4/2005 | Rezai |
| 6,912,419 B2 | 6/2005 | Hill et al. |
| 6,922,590 B1 | 7/2005 | Whitehurst |
| 7,076,292 B2 | 7/2006 | Forsberg |
| 7,149,574 B2 | 12/2006 | Yun et al. |
| 7,155,278 B2 | 12/2006 | King et al. |
| 7,236,822 B2 | 6/2007 | Dobak, III |
| 7,239,912 B2 | 7/2007 | Dobak, III |
| 7,433,734 B2 | 10/2008 | King |
| 7,483,746 B2 | 1/2009 | Lee et al. |
| 7,529,582 B1 | 5/2009 | DiLorenzo |
| 7,551,964 B2 | 6/2009 | Dobak, III |
| 7,599,736 B2 | 10/2009 | DiLorenzo |
| 7,771,382 B2 | 8/2010 | Levine et al. |
| 2002/0032177 A1 | 3/2002 | Allan et al. |
| 2002/0065217 A1 | 5/2002 | Qian et al. |
| 2002/0072780 A1 | 6/2002 | Foley |
| 2002/0077675 A1 | 6/2002 | Greenstein |
| 2002/0099419 A1 | 7/2002 | Cohen et al. |
| 2003/0008838 A1 | 1/2003 | Havel et al. |
| 2003/0014127 A1 | 1/2003 | Talja et al. |
| 2003/0045909 A1 | 3/2003 | Gross et al. |
| 2003/0144708 A1 | 7/2003 | Starkebaum |
| 2003/0181958 A1 | 9/2003 | Dobak, III |
| 2003/0191476 A1 | 10/2003 | Smit |
| 2003/0211967 A1 | 11/2003 | Bryant et al. |
| 2004/0015201 A1 | 1/2004 | Greenstein |
| 2004/0039452 A1 | 2/2004 | Bessler |
| 2004/0049209 A1 | 3/2004 | Benchetrit |
| 2004/0089313 A1 | 5/2004 | Utley et al. |
| 2004/0097989 A1 | 5/2004 | Molina Trigueros |
| 2004/0107004 A1 | 6/2004 | Levine et al. |
| 2004/0230255 A1 | 11/2004 | Dobak, III |
| 2004/0249362 A1 | 12/2004 | Levine et al. |
| 2004/0249416 A1 | 12/2004 | Yun et al. |
| 2005/0065575 A1 | 3/2005 | Dobak |
| 2005/0080395 A1 | 4/2005 | Levine et al. |
| 2005/0080491 A1 | 4/2005 | Levine et al. |
| 2005/0125020 A1 | 6/2005 | Meade et al. |
| 2005/0143788 A1 | 6/2005 | Yun et al. |
| 2005/0149146 A1 | 7/2005 | Boveja et al. |
| 2005/0192614 A1 | 9/2005 | Binmoeller |
| 2006/0178691 A1 | 8/2006 | Binmoeller |
| 2007/0162085 A1* | 7/2007 | DiLorenzo ............... 607/40 |
| 2008/0262411 A1 | 10/2008 | Dobak |
| 2009/0259279 A1 | 10/2009 | Dobak, III |
| 2010/0216709 A1 | 8/2010 | Scheule et al. |

FOREIGN PATENT DOCUMENTS

| | | |
|---|---|---|
| WO | WO 95/28783 | 10/1995 |
| WO | WO 98/53878 | 12/1998 |
| WO | WO 98/57701 | 12/1998 |
| WO | WO 00/61223 | 10/2000 |
| WO | WO 01/52932 | 7/2001 |
| WO | WO 01/58520 | 8/2001 |
| WO | WO 01/83028 | 11/2001 |
| WO | WO 02/04068 | 4/2002 |
| WO | WO 02/26315 | 4/2002 |
| WO | WO 02/26317 | 4/2002 |
| WO | WO 02/34331 | 5/2002 |
| WO | WO 02/43467 | 6/2002 |
| WO | WO 02/062291 | 8/2002 |
| WO | WO 03/086246 | 10/2003 |
| WO | WO 03/094785 | 11/2003 |
| WO | WO 2004/019765 | 3/2004 |
| WO | WO 2004/049982 | 6/2004 |
| WO | WO 2004/064680 | 8/2004 |
| WO | WO 2004/064685 | 8/2004 |
| WO | WO 2006/007048 | 1/2006 |
| WO | WO 2006/023498 | 3/2006 |
| WO | WO 2007/087332 | 8/2007 |
| WO | WO 2007/146287 | 12/2007 |

OTHER PUBLICATIONS

Adrian, T.E., et al, "Distributionand postprandial release of porcine peptide YY." J. Endocr., 1987, 113:11-14, Journal of Endocrinology Ltd., Great Britain.

Adrian, T.E., et al., "Human Distributionand Release f a Putative New Gut Hormone, Peptide YY," Gastroenterology, Nov. 1985, 89:1070-7, American Gastroenterioaical Association.

Ahren, B., "Autonomic regulation of islet hormone secretion—Implications for health and disease," Diabetolgia, (2000) 43: 393-410.

Ahren, B., "Sympathetic Nerve Stimulation Versus Pancreatic Norepinephrine Infusion in the Dog: 1)Effects on Basal Release of Insulin Glucagon," Endocrinoiogy, Mar. 1986, pp. 323-331, vol. 121, No. 1.

Alamo, et al., "Electrically-Evoked Catecholamine Release from Cat

Adrenals, Biochemical Pharmacology," (1991), vol. 42, No. 5, pp. 973-978.

Alvarez, et al., "Sympathetic Neural Activation in Visceral Obesity, Circulation," Nov. 12, 2002, pp. 2533-2536.

Amar, Al, "Vagus Nerve Stimulation for intractable Epilepsy," Cyberonics Brochure; Pub. Date unknown; thirteen pages.

Andrews, P.L.R., et al., "Interactions Between Splanchnic and Vagus Nerves in the Control of Mean Intragastric Pressure in the Ferret," J. Physiol., 351: 473-490, 1984.

Andrews, Russell J., "Neuromodulation I. Techniques—Deep Brain Stimulation, Vagus Nerve Stimulation, and Transcranial Magnetic Stimulation," Ann. N.Y. Acad. Sci. 993: 1-13 (2003).

Ballard, K., et al., "The Unresponsiveness of Lipid Metabolism in Canine Mesenteric Adipose Tissue to Biogenic Amines and to Sympathetic Nerve Stimulation," Acta Physiol. Scan. 1969: 77, 442-448.

Barone, Frank C, et al. "Gastric Distension Modulates Hypthalamic Neurons Via a Sympathetic Afferent Path Through the Mesencephalic Periaqueductal Gray," Brain Research Bulletin, vol. 38, No. 3, pp. 239-251, 1995.

Becker, M.D., James M., et al., "Myoelectric control of gastrointestinal and biliary motility: A review," Surgery vol. 89, No. 4: 466-477, 1981.

Binks, et al., "High Strength Stimulation of the Vagus Nerve in Awake Humans: A Lack of Cardiorespiratory Effects," Respiration Physiology, vol. 127, (2001), pp. 125-133.

Birks, R.I., "Regulation by Patterned Preganglionic Neural Activity of Transmitter Stores in a Sympathetic Ganglion," J. Physiol., (1978), 280, pp. 559-572.

Blackshaw, L.A.,et al., "Vagal and sympathetic influences on the ferret lower oesophageal sphincter," Journal of the Autonomic Nervous System, 66: 179-188, 1997.

Bloom, S., "The Adrenal Contribution to the Neuroendocrine Responses to Splanchnic Nerve Stimulation in Conscious Calves," Journal of Physiology, Jul. 1987, pp. 513-526, vol. 397.

Bolte, E. et al., "Steroid Production from Plasma Cholesterol. II In Vivo Conversion of Plasma Cholesterol to Ovarian Progesterone and Adrenal C10 and C21 Steroids in Humans", JCE&M, vol. 38, No. 3,(1974), pp. 394-400.

Bray, G., "Reciprocal Relation of Food Intake and Sympathetic Activity: Experimental Observations and Clinical Implications," International Journal of Obesity, 2000, pp. S8-S17, vol. 24, Suppl. 2.

Brillon, D., "Effect of Cortisol on Energy Expenditure and Amino Acid Metabolism in Humans," American Journal of Physiology, May 1994, pp. E501-E513, vol. 268.

Brown, et al., "Changes in Food Intake with Electrical Stimulation of the Ventromedial Hypothalamus in Dogs." J Neurosurg, vol. 60, Jun. 1984, pp. 1253-1257.

Buckley, et al., "Circulatory Effects of Splanchnic Nerve Stimulation in Developing Swine," The American Physiological Society, (1996), pp. H69-H74.

Bugbee, Martin, et al., "Design of a Selective Nerve Stimulator," Webpage, 1996.

Castiglione, K.E., et al., "Food Intake Responses to Upper Gastrointestinal Lipid Infusions in Humans," Physiology & Behavior, 1998, 64(2): 141-5.

Chen, Ke et al., "Induction of Leplin Resistance Through Direct Interaction of C-Reactive Protein with Leptin", Nature Medicine, vol. 12. No. 4,(2006), pp. 425-432.

Cigaina, et al., "Gastric Peristalsis Control by Mono Situ Electrical Stimulation: a Preliminary Study," Obesity Surgery, 6, (1996), pp. 247-249.

Cigaina, et al., "Long-Term Effects of Gastric Pacing to Reduce Feed Intake in Swine," Obesity Surgery, 6, (1996), pp. 250-253.

Clutter, W., "Epinephrine Plasma Metabolic Clearance Rates and Physiologic Thresholds for Metabolic and Hemoduynamic Actions in Man," Journal of Clinical Investigation, Jan. 1980, pp. 94-101, vol. 66.

Cottrell, D.F., et el., "Tension receptors with vagal afferent fibres in the proximal duodenum and pyloric sphincter of sheep," J Physiol., 1984, 354:457-75 Great Britain.

Crago, et al., "The Choice of Pulse Duration for Chronic Electrical Stimulation via Surface, Never, and Intramuscular Electrodes," Annals of Biomedical Engineering, 2, (1974) pp. 252-264.

Cummings, D., "Plasma Ghrelin Levels after Diet-Induced Weight Loss or Gastric Bypass Surgery," The New England Journal of Medicine, May 2002, pp. 1623-1630, vol. 346, No. 21.

Cuschieri, A., "Bilateral Endoscopic Splanchnicectomy through a Posterior Thorascopic Approach," J. R. Coll. Surg. Edinb., Feb. 1994, pp. 44-47, vol. 39.

Delbro, B. et al., "Non-ganglionic cholinergic excitatory pathways in the sympathetic supply to the feline stomach." Acta Physiol Scand, 110: 137-144, 1980.

Deloof, S., "Sympathetic control of antral and pyloric electrical activity in the rabbit," Journal of the Autonomic Nervous System, 22: 1-10, 1986.

Dodt, C. et al. "Sympathetic Control of White Adipose Tissue in Lean and Obese Humans," Acta Physiol. Scan. 2003, 177, 351-357.

Dodt, C., et al., "The Subcutaneous Lipolytic Response to Regional Neural Stimulation in Reduced in Obese Women," Diabetes, vol. 49, Nov. 2000.

Dodt, Christoph, et al., "Intraneural Stimulation Elicits an Increase in Subcutaneous Interstitial Glycerol Levels in Humans," Journal of Physiology (1999), 521.2, pp. 545-552.

Dunning, et al., "Pancreatic and Extrapancreatic Galanin Release During Sympathetic Neural Activation," Am J Physiol Endocrinol Metab, Mar. 1990, 258: pp. 436-444.

Edwards, A. "Adrenal Catecholamine Output in Responses to Stimulation of the Splanchnic Nerve in Bursts in the Conscious Calf," Journal of Physiology, Sep. 1981, pp. 409-419, vol. 327.

Edwards, A., "Adrenal Medullary Responses to Stimulation of the Splanchnic Nerve in the Conscious Calf," Journal of Physiology, Jan. 1980, pp. 15-27, vol. 308.

Edwards, A., "The Effect of Splanchnic Nerve Stimulation on Adrenocortical Activity in Conscious Calves," Journal of Physiology, Apr. 1986, pp. 385-396, vol. 382.

Edwards. A., "The Glycogenolytic Response to Stimulation of the Splanchnic Nerves in Adrenalectomized Calves, Sheep, Dogs, Cats, and Pigs," Journal of Physiology, Nov. 1970, pp. 741-759, vol. 213.

Edwards, A.V., "The Sensitivity of the Hepatic Gylocogenolytic Mechanism to Stimulation of the Splanchnic Nerves," J. Physiol (1972), 220, pp. 315-334.

Edwards, et al., "The Effect of Splanchnic Nerve Stimulaton on the Uptake of Atrial Natriuretic Peptide by the Adrenal Gland in Conscious Calves," J. Endocrinol. Invest. 13, (1990), pp. 887-892.

Eissele, R. et al., "Glucagon-like peptide-1 cells in the gastrointestinal tract and pancreas of rat, pig, and man," European Journal of Clinical investioation, 1992, 22:283-91.

Engeland, W., "Splanchnic Nerve Stimulation Modulates Steriod Secretion in Hypophysectomized Dogs," Neuroendocrinology, Aug. 1988, pp. 124-131, vol. 50.

Fang, Zi-Ping, et al., "Alternate excitation of large and small axons with different stimulation waveforms: an application to muscle activation," Med. & Bio. Eng. & Comput., 29:543-547, 1991.

Feinle, C., et al., "Effects of duodenal fat, protein or mixed-nutriet infusions on epigastric sensations during sustained gastric distension in healthy humans," Neurogastroenterol Mot., 2002, 14:205-13, Blackwell Science Ltd.

Feinle, C., et al., "Modulation of gastric distension-induced sensations by small intestinal receptors," Am J Physiol Gastrointest Liver Physiol, 2001, 280:G51-7.

Feinle, C., et al., "Relationship between increasing duodenal lipid doses, gastric perception, and plasma hormone levels in humans," Am J Physiol egulatory Intergratve Comp Physiol, 2000, 278:R1217-23. The American Physiological Soceity.

Feinle, C., et al, "Role of duodenal lipid and cholecystokinin A receptors in the pathophysiology of functional dyspspsia," Gut, 2001, 48:347-55.

Final Office Action received for U.S. Appl. No. 10/785,726, Mailed on Dec. 24, 2008, pp. 11.

Final Office Action received for U.S. Appl. No. 10/785,726, Mailed on Feb. 4, 2008, pp. 5.

Final Office Action received for U.S. Appl. No. 10/785,726, Mailed on May 22, 2008, pp. 8.

Final Office Action received for U.S. Appl. No. 10/920,734, Mailed on Apr. 1, 2009, pp. 8.

Final Office Action received for U.S. Appl. No. 11/422,019, Mailed on Jun. 29, 2009, pp. 13.
Fink, A.S., et al., "Release of Human Pancreatic Polypeptide and Gastrin in Response to Intrduodenal Stimuli: A Case Report," Metabolism, Apr. 1979, 29(4): 339-42.
Fox, E.S., et al.. "Neurotrophin-4 Deficient Mice Have a Loss of Vagal Intraganglionic Mechanoreceptors from the Small Intestine and a Disruption of Short-Term Satiety," Journal of Neuroscience, Nov. 1, 2001, 21(21):8602-15.
Fredholm, B.B. "Effects of Vasoactive Drugs on Circulation in Canine Subcutaneous Adipose Tissue," Acta Physiol. Scand. 1970, 79, 564-574.
Friesen , et al., Canadian Journal of Physiology and Pharmacology, The National Research Council of Canada, vol. 49, May 1971, No. 5, pp. 375-381.
Fukushima, K., et al., "Differential Blocking of Motor Fibers by Direct Current," Pflugers Arch. 358:235-242, 1975.
Furness, J., "Effects of Vagal and Splanchnic Section on Food Intake, Weight, Serum Lepin, and Hypothalamic Neuropeptide Y in Rat," Autonomic Neuroscience: Basic and Clinical, Feb. 2001, pp. 28-36, vol. 92.
Gy, Xu, et al., "Modulation of hypothalamic arcuate nucleus on gastric motility in rats," World J. Gastroenterol, 1998, http://wjgnet.com, 4(5): 426-429.
Hak, et al., "Associations of C-Reactive Protein With Measures of Obesity, Insulin resistance and Subclinicai Atherosclerosis in Healthy, Middle-Aged Women," American heart Association, Arteriosclerosis, Thombosis and Bascular Biology, 1999; 19, 1986-1991.
Hammond, et al., "Vagus Nerve Simulation in Humans: Neurophysiological Studies and Electrophysiological Monitoring," Epilepsia, vol. 31, Suppl. 2, (1990), pp. S51-S59.
Heck, et al., "Vagus Nerve Stimulation Therapy, Epilepsy, and Device Parameters." Neurology 59, Suppl 4, Sep. 2002, pp. S31-S37.
Holst, et al., "Nervous Control of Pancreatic Exocrine Secretion in Pigs," Acta Physiol. Scand., (1979) 105, pp. 33-51.
Hopp, F.A., et al., "Effect of anodal blockade of myelinated fibers on vagal C-fiber afferents," The American Physiologicai Society, 1980.
International Preliminary Report on Patentability for PCT Patent Application No. PCT/US2007/01847, mailed on Aug. 7, 2008, pp. 12.
International Search Report for PCT Patent Application No. PCT/US2000/40301, Mailed on Jan. 10, 2001, pp. 2.
International Search Report for PCT Patent Application No. PCT/US2001/00983, Mailed on May 9, 2001, pp. 3.
International Search Report for PCT Patent Application No. PCT/US2001/03319, Mailed on Jun. 12, 2001, p. 1.
International Search Report for PCT Patent Application No. PCT/US2001/29892, Mailed on Mar. 13, 2002, p. 1.
International Search Report for PCT Patent Application No. PCT/US2001/29914, Mailed on Feb. 27, 2002, p. 1.
International Search Report for PCT Patent Application No. PCT/US2004105057, Mailed on Feb. 15, 2006, pp. 2.
International Search Report for PCT Patent Application No. PCT/US2005/29126, Mailed on Feb. 2, 2006, pp. 1.
International Search Report for PCT Patent Application No. PCT/US2007/01847, Mailed on Nov. 19, 2007, 1 page.
International Search Report for PCT patent Application No. PCT/US2007/13780, Mailed on Sep. 23, 2008, 1 page.
Itina, L.V., "Sympatho-activatory and sympatho-inhibitory afferent fibers of vagus and splanchnic nerves." Sechenov Physiological Journal of the USSR, Institute of Physiology Acad. Sci. Belorus, SSR, Minsk, 1979, (Russian text with English abstract).
Itina, L.V., et al., "Impulsation of the spianchnic and vagus nerves after introduction of fat into the lumen of the small intestine," Sechnov Physiologicai Journal of the USSR, Institute of Physiology Acad. Sci. BSSR, Minsk, 1972.
Ito, Shigeo, et al., "Gastric Vasodilator and Motor Response to Splanchnic Stimulation and Tachykinins in the Dog," Gen. Pharmac, vol. 24, No. 2: 291-298, 1993.
Jarhult, M.D., et al., "The Functional Importance of Sympathetic Nerves to the Liver and Endocrine Pancreas," Ann. Surg., Jan. 1979, vol. 189, No. 1. p. 96-100.

Jaw, F.-S. et al., "A modified "triangular pulse" stimulator for C-fibers stimulation," Journal of Neuroscience Methods, 37:169-172, 1991.
Jonson, et al., "Splanchnic Nerve Stimulation Inhibits Duodenal HCO3 Secretion in the Rat," American Physiological Society, (1988), pp. G709-G712.
Jorum, et al., "Analgesia by low-frequency nerve stimulation mediated by low-threshold afferents in rats," Pain, 32 (1988) 357-366.
Kaneto, A., et al., "Effect of splanchnic nerve stimulation on glucagons and insulin output in the dog," Endocrinolgy Jan. 1975; 96(1): 143-50.
Katzeff, H., "Metabolic Studies in Human Obesity during Overnutrition and Undernutrition: Thermogenic and Hormonal Responses to Norepinephrine," Metabolism, Feb. 1986, pp. 166-175, vol. 35, No. 2.
Koo, et al., "Human Vagus Nerve Electrophysiology," J Clin Neurophysiol, Sep. 2001, 18(5), pp. 429-433.
Kral, et al., "Gastrophlasty for Obesity:Long-Term Weight Loss Improved by Vagotomy," World Journal of Surgery, vol. 17, No. 1, Jan./Feb. 1993, pp. 17 and 75-79.
Kuo, D., "A Wide Field Electron Microscopic Analysis of the Fiber Constituents of the Major Splanchnic Nerve in Cat," The Journal of Comparative Neurology, Apr. 1982, pp. 49-58, vol. 210.
Kurose, T. et al., "Gulcagon, insulin and somatostatin secretion in response to sympathetic neuralactivation in streptozotocin-induced diabetic rats. A study with the isolatedperfused rat pancreas in vitro.," Diabetologia Nov. 1992; 35(11): 1035-41.
Kurose, T., "Mechanism of Sympathetic Neural Regulation of Insulin, Somatostatin, and Glucagon Secretion," American Journal of Physiology, Mar. 1989, pp. E220-E227, vol. 258.
Leibel, R., "Changes in Energy Expenditure Resulting from Altered Body Weight," The New England Journal of Medicine, Mar. 1995, pp. 621-628, vol. 332, No. 10.
Lemieux, et al., "Elevated C-Reactive Protein: Another Component of the Artherothrombotic Profile of Abdominal Obseity," American Heart Association, Arteriosclerosis, Thrombosis and Vascular Biology, 2001; 21; 961-967.
Lerman, M.D., Sheldon H., et al., "Gastric Motor Response to Sympathetic Nerve Stimulation," Journal of Surgical Research 32: 15-23, 1982.
Lerman, M.D., Sheldon H., et al., "Pyloric motor response to sympathetic nerve stimulation in dogs," Surgery vol. 89, No. 4: 460-465, 1981.
Lingenfelser, T., et al., "Effects of duodenal distension on antropyloroduodenal pressures and perception are modified by hyperglycemia," Am J Physiol, 1999, 276, G711-G718.
Lloyd, K.C., et al., "Duodenal lipid inhibits gastric acid secretion by vagal, capsaicin-sensitive afferent pathways in rats," Am J Physiol., 1993, 27:G659-63.
Lockard, et al., "Feasibility and Safety of Vagal Stimulation in Monkey Model," Epilepsia, vol. 31, Suppl. 2, (1990), pp. S20-S26.
MacDonald, K.G., et al., "The Gastric Bypass Operation educes the Progression and Mortality of Non-Insulin-Dependent Diabetes Mellitus," J Gastrointest Surg, May 1, 1997, 1(3):213-220.
Maddison, S., et al., "Hypothalamic Unit Responses to Alimentary Perfusions in the Anesthetised Rat," Brain Research Bulletin, 1979, 4(2); 259-66.
Matthews, D., "Effect of Epinephrine on Amino Acid and Energy Metaboiism in Humans," American Journal of Physiology, Sep. 1989, pp. E948-E956, vol. 258.
Mirkin, B., "Factors influencing the Selective Secretion of Adrenal Medullary Hormones," Journal Pharmacol. Exp. Ther., Oct. 1960, pp. 218-225, vol. 132.
Mokdad, A., "The Continuing Epidemics of Obesity and Diabetes in the United States." Journal of the American Medical Association, Sep. 2001, pp. 1195-1200, vol. 286, No. 10.
Monroe, MB, et al., "Direct Evidence for Tonic Sympathetic Support of Resting Metabolic Rate in Healthy Adult Humans," Am. J. Physiol Endocrinol Metab. 280:E740-E744, 2001.
Naidoo, N., "Thoracic Splanchnic Nerves: Implications for Spianchnic Denervation," Journal of Anatomy, Jun. 2001, pp. 585-590, vol. 199.

Nakazato, Yoshikazu, et al., "Atropine- and hexinethonium-resistant motor response to greater splanchnic nerve stimulation in the dog stomach," Journal of the Autonomic Nervous System, 20:35-42, 1987.

Nakazato, Yoshikazu, et al., "Gastric Motor and Inhibitor Response to Stimulation of the Sympathetic Nerve in the Dog," Jap. J. Pharmac, 20: 131-141, 1970.

Non-Final Office Action received for U.S. Appl. No. 10/785,726, Mailed on Jul. 25, 2007, pp. 9.

Non-Final Office Action received for U.S. Appl. No. 10/920,734, Mailed on Jun. 30, 2008, pp. 6.

Non-Final Office Action received for U.S. Appl. No. 10/920,734, Mailed on Aug. 7, 2009, pp. 12.

Non-Final Office Action received for U.S. Appl. No. 11/338,388, Mailed on Apr. 16, 2009, pp. 9.

Non-Final Office Action received for U.S. Appl. No. 11/422,019, Mailed on Nov. 19, 2008, pp. 3.

Non-Final Office Action received for U.S. Appl. No. 11/657,877, Mailed on Jun. 19, 2009. pp. 14.

Notice of Allowance received for U.S. Appl. No. 10/785,726, Mailed on May 14, 2009. pp. 8.

Office Action received for Australian Patent Application No. 2004216247, Mailed on Sep. 25, 2008, 2 pages.

Office Action received for Japanese Patent Application No. 2006-503742, Mailed on Aug. 12, 2009, 2 pages of Office Action and English translation of 2 pages.

Opsahl, Charles A., "Sympathetic nervous system involvement in the lateral hypothalamic lesion syndrome," Department of Psychology, Yale University, New Haven Connecticut 06520, Jul. 7, 1976.

Oro, Lars, et al. "Influence of Electrical Supramedullary Stimulation on the Plasma Level of Free Fatty Acids, Blood Pressure and Heart Rate in the Dog," Acta Medica Scandinavica, vol. 178, fasc. 6, 1965.

Pan, et al., "Role of Summation of Afferent input in Cardiovascular Reflexes from Splanchnic Nerve Stimulation," The American Physiological Society, (1996) pp. H849-H856.

Peterson, H. "Body Fat and the Activity of the Autonomic Nervous System," The New England Journal of Medicine, Apr. 1988, pp. 1078-1083, vol. 318, No. 17.

Pilichiewicz, A., et al., Effect of lipase inhibition on gastric emptying of, and the glycemic and incretin responses to, an oil/aquenos drink in type 2 diabetes mellitus, J Clin Endocrinol Metab, 2003, 88:3829-34.

Ratheiser, K., "Epinephrine Produces a Prolonged Elevation in Metabolic Rate in Humans," American Journal of Nutrition, Oct. 1997, pp. 1046-1052, vol. 68.

Ravussin, E., "Reduced Rate of Energy Expenditure as a Risk Factor for Body-Weight Gain," The New England Journal of Medicine, Feb. 1998, pp. 467-472, vol. 318, No. 8.

Reidelberger, R.D., et al., "Postgastrio satiety in the sham-feeding rat," Am J Physiol Regulatory Intergrative Comp Physiol, 1983, 244:672-81.

Rosell, S., "Release of Free Fatty Acids From Subcutaneous Adipose Tissue in Dogs Following in Canine Mesenteric Adipose Tissue in Dogs Following Sympathetic Nerve Stimulation," Acta Physiol. Scan. 1966, 67, 343-351.

Rozman, et al., "Multielectrode Spiral Cuff for Selective Stimulation of Nerve Fibers," Journal of Medical Engineering & Technology, vol. 16, No. 5, (Sep. Oct. 1992), pp. 194-203.

Rozman, J., et al., "Recording of ENGs from the nerves innervating the pancreas of a dog during the intravenous glucose tolerance test," National Library of Medicine, Physiol Meas., Nov. 2002, 23(4):695-705.

Rozman, Janez, et al., "Recording of Electroneurograms from the Nerves Innervating the Pancreas of a Dog," Journal of Neuroscience Methods, 112 (2001) 155-162.

Rozman, Janez, et al., "Stimulation of Nerves Innervating the Dog's Pancreas," Artificial Organs 26(3): 241-243.

Sato, T, et al., "Novel therapeutic strategy against central baroreflex failure: a bionic baroreflex system," National Library of Medicine, Jul. 20, 1999: 100(3)299-304.

Shafik, A., "Effect of Duodenal Distension on the Pyloric Sphincter and Antrum and the Gastric Corpus: Duodenopyloric Relfex," World J Surg, 1998, 22:1061-4.

Shimazu, T., "Central Nervous System Regulation of Liver and Adipose Tissue Metabolism," Diabetologia, (1981) 20: 343-356.

Sjostrom, L., "Epinephrine Sensitivity with respect to Metabolic Rate and Other Variables in Women," American Journal of Physiology, Sep. 1982, pp. E431-E442, vol. 245.

Staten, M., "Physiological increments in Epinephrine Stimulate Metabolic Rate in Humans," American Journal of Physiology, Nov. 1986, pp. E322-E330, vol. 253.

Stoddard, et al., "Adrenal Medullary Secretion with Splanchnic Stimulation in Spinal Cats," Journal of the Autnomic Nervous System, 38 (1992), pp. 105-116.

Strickland, T., "Performance of Local Anesthetic and Placebo Splanchnic Blocks via Indwelling Catheters to Predict Benefit from Thoracoscopic Splanchnicectomy in a Patient with Intractable Pancreatic Pain," Anesthesiology, Jun. 1995, pp. 980-983, vol. 84.

Sweeney, James D., et al., "An Asymmetric Two Electrode Cuff for Generation of Unidirectionally Propagated Action Potentials," IEEE Transaction on Biomedical Engineering, vol. BME-33, No. 6: 541-549, 1986.

Tataranni, P., "From Physiology to Neuroendocrinology: A Reappraisal of Risk Factors of Bodt Weight Gain in Humans," Diabetes & Metabolism, Oct. 1997, pp. 108-115, vol. 24, No. 2.

Terry, et al., "An Implantable Neurocybernetic Prosthesis System, Epilepsia," vol. 31, Suppl. 2, (1990), pp. S33-S37.

Thoren, Peter, et al., "Anodal block of medullated cardiopulmonary vagal afferents in cats," J. Appl. Physiol.: Respir. Environ. Exercise Physiol. 42: 461-465, 1977.

Tran, M.A., et al., "Adrenergic Neurohumoral Influences of FFA Release From Bone Marrow Adipose Tissue," J. Pharmacol (Paris), 1985, 16, 2, 171-179.

U.S. Appl. No. 60/729,770, entitled Biliary/Pancreatic Shunt Device and Method for Treatment of Metabolic and other Diseases filed Oct. 24, 2005.

University of Florida Research and Graduate Programs (RGP) website http://rgp.ufl.edu/otl/viewTech.html, "Method and Apparatus for Allowing Selective Activity in Small Diameter Nerve Fibers."

Upton, et al., "Autonomic Stimulation," PACE, vol. 14, Jan. 1991, pp. 50-69.

Van Den Honert, et al., "A Technique for Collision Block of Peripheral Nerve: Single Stimulus Analysis," IEEE Transactions on Biomedical Engineering, vol. BME-28, No. 5, May 1981, pp. 373-378.

Van Den Honert, et al., "Generation of Unidirectionally Propagated Action Potentials in a Peripheral Nerve by Brief Stimuli," Science, voi. 206, Dec. 14, 1979, pp. 1311-1312.

Visser, et al., "Elevated C-Reactive Protein levels in Overweight and Obese Adults," JAMA, 1999: 282(2): 2131-2135.

Wilkinson, H., "Precutaneous Radiofrequency Upper Thoracic Sympathectomy," Neurosurgery, Aug. 1994, pp. 715-725, vol. 38, No. 4.

Woodbury, et al., "Effects of Vagal Stimulation on Experimentally Induced Seizures in Rats," Epilepsia, vol. 31, Suppl. 2, (1990), pp. S7-S19.

Wu, et al., "Expression of bitter taste receptors of the T2R family in the gastrointestinal tract and enteroendocrine STC-1 cells," Proc Natl Acad Sci U S A, 2002, 99, 2392-97.

* cited by examiner

PULSE GENERATOR SCHEMATIC

CATHETER-TYPE LEAD/ELECTRODE ASSEMBLY

FIG DD1A
Algo A – Diurnal 30/60
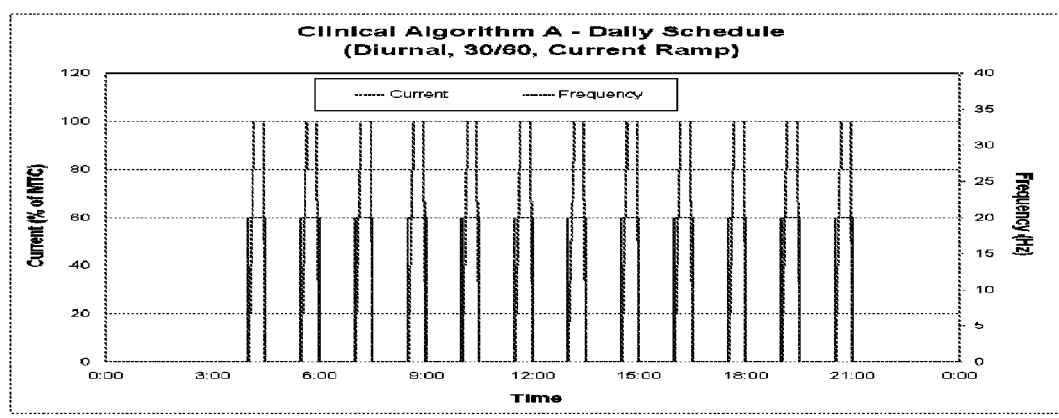
FIG DD1B
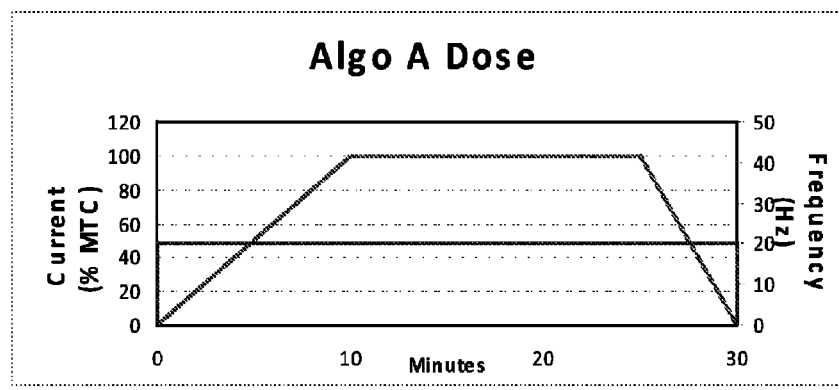

FIG DD2
Anesthetized Dosing
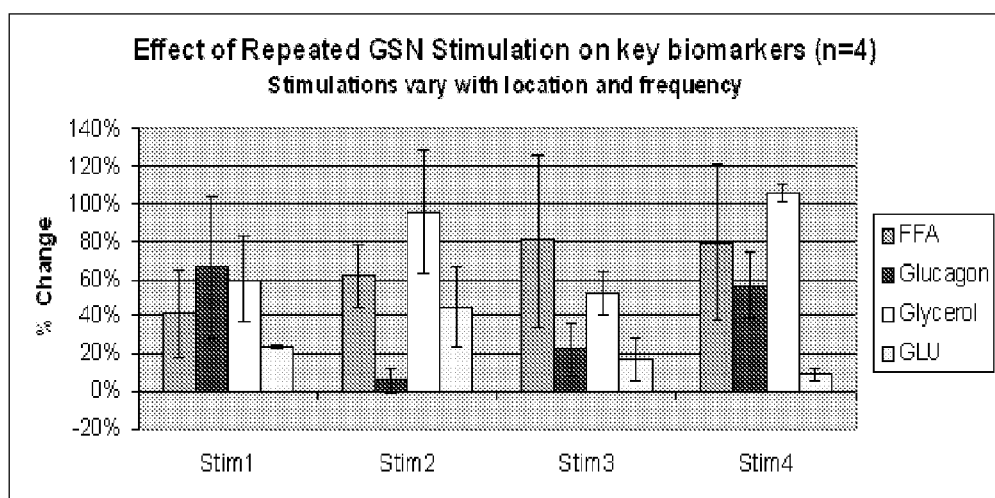
- Serial Stimulations (4 dogs/4 doses each)
  - Dose parameters (variable) 5-7 minutes of stim
- 25-30min off time

FIG DD3
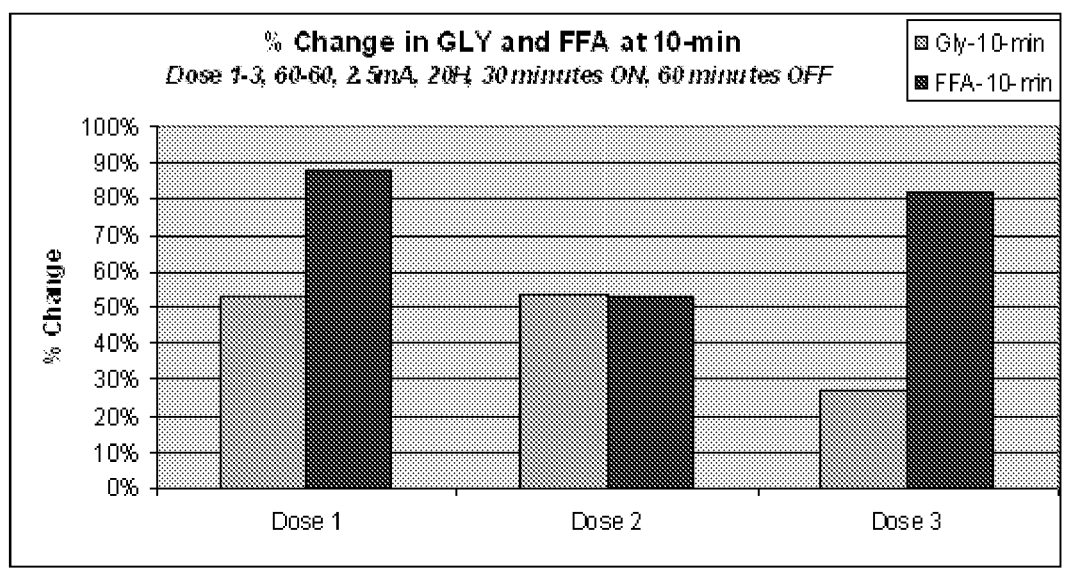
30/60 Dosing
- Consistent stim parameters
- 2.5mA/20Hz
- Specific 30/60 serial activations FIG DD4
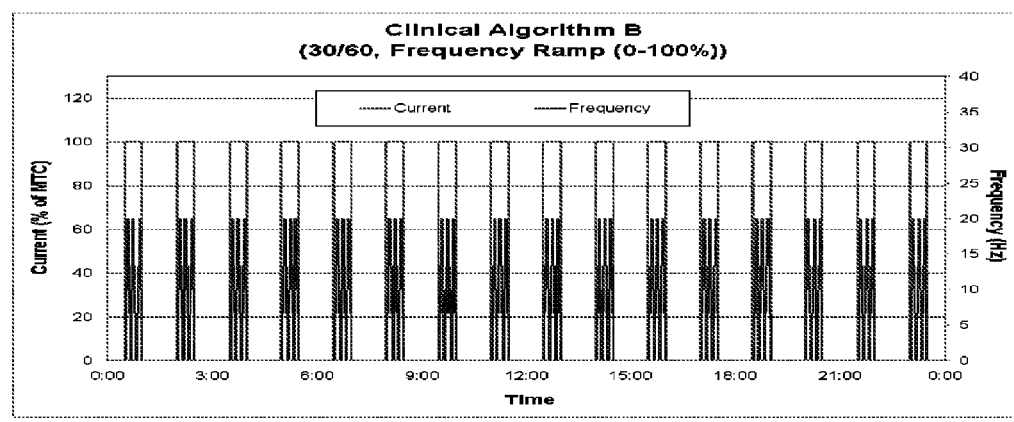
FIG DD5
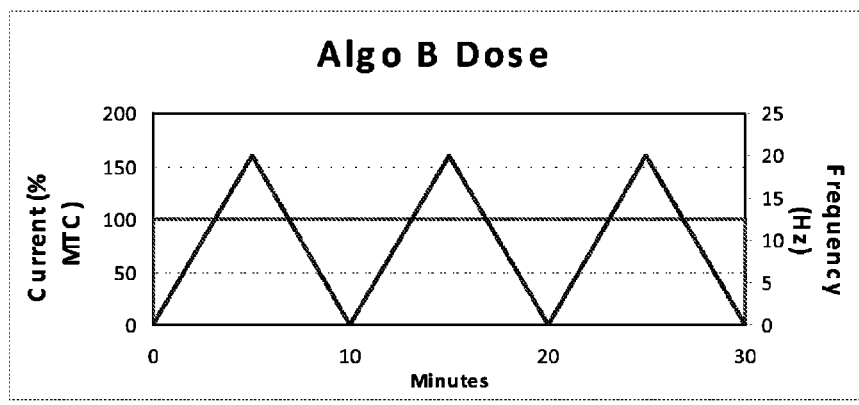

FIG DD6
Algorithm C
Alternative Freq Ramp
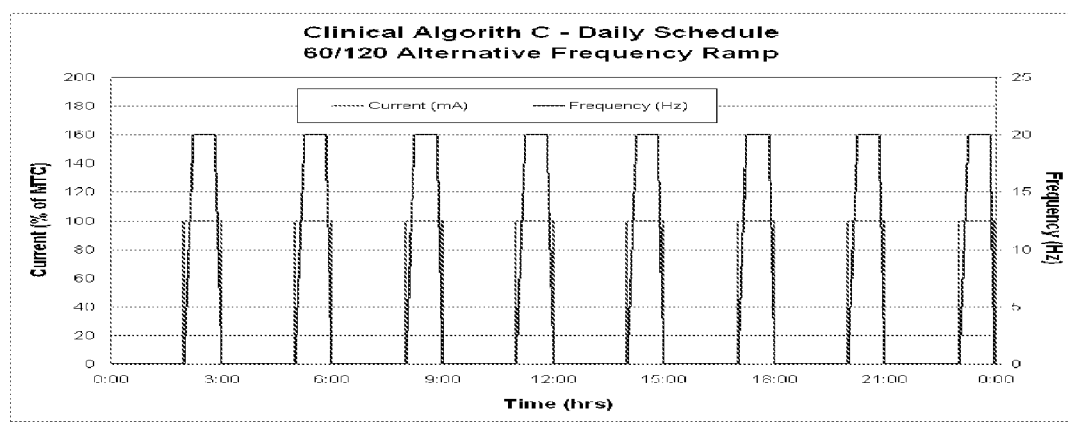
FIG DD7
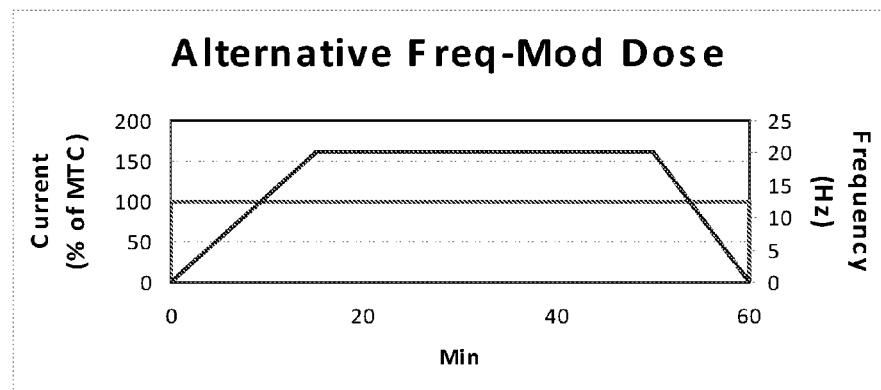

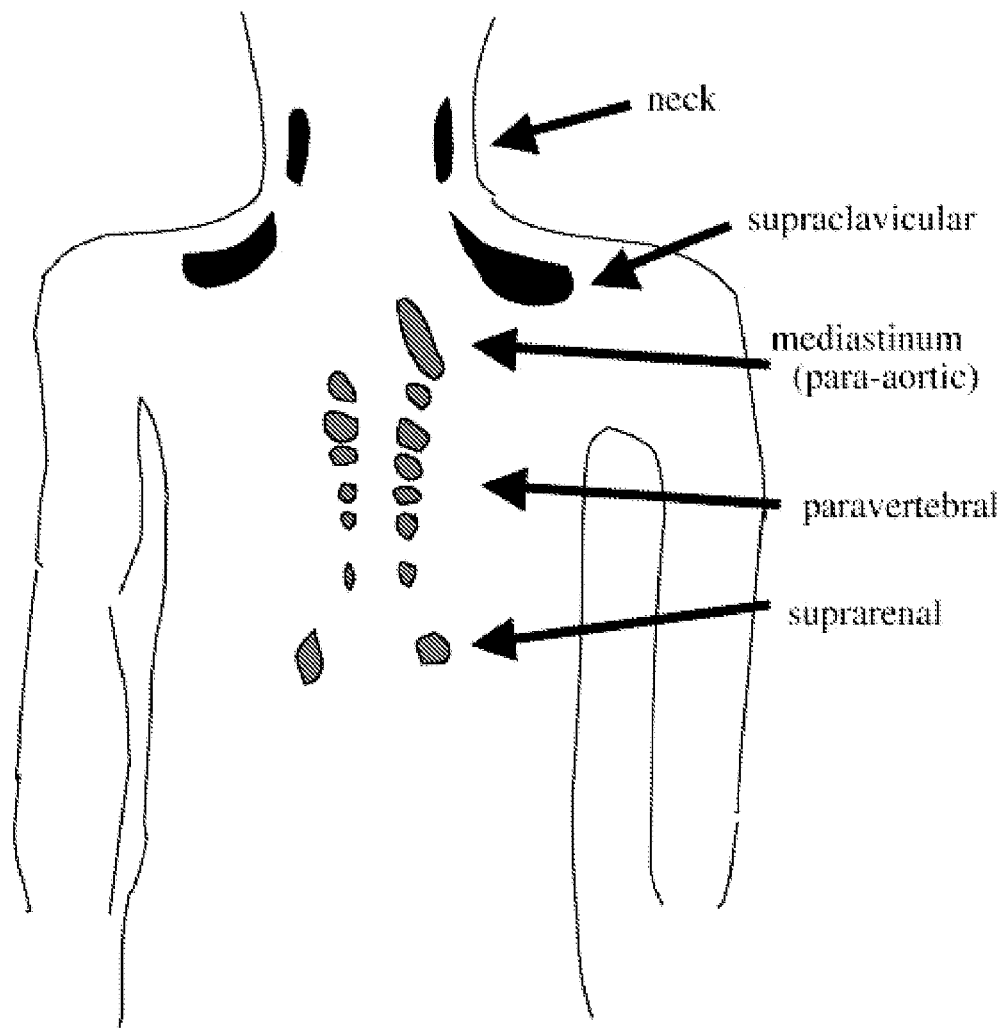
FIG XXX

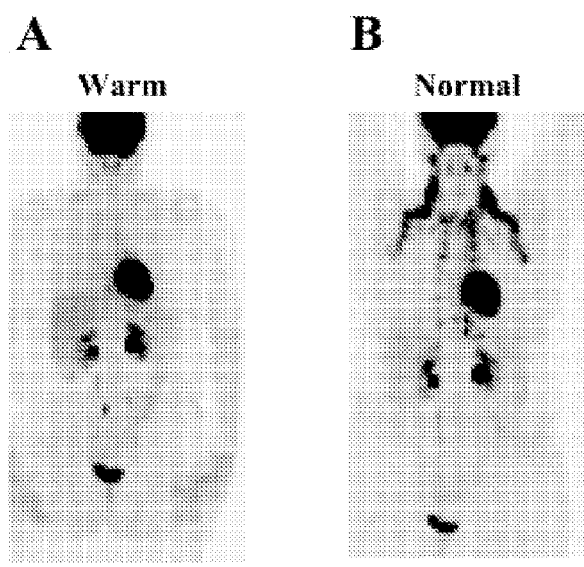
FIG YYY
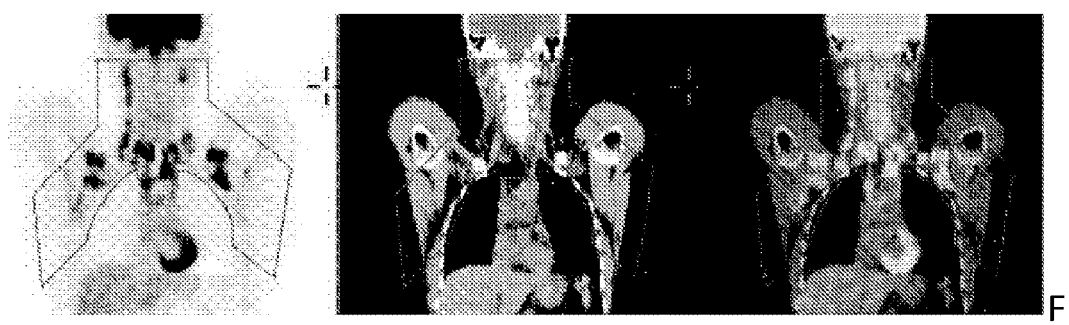
FIG ZZZ

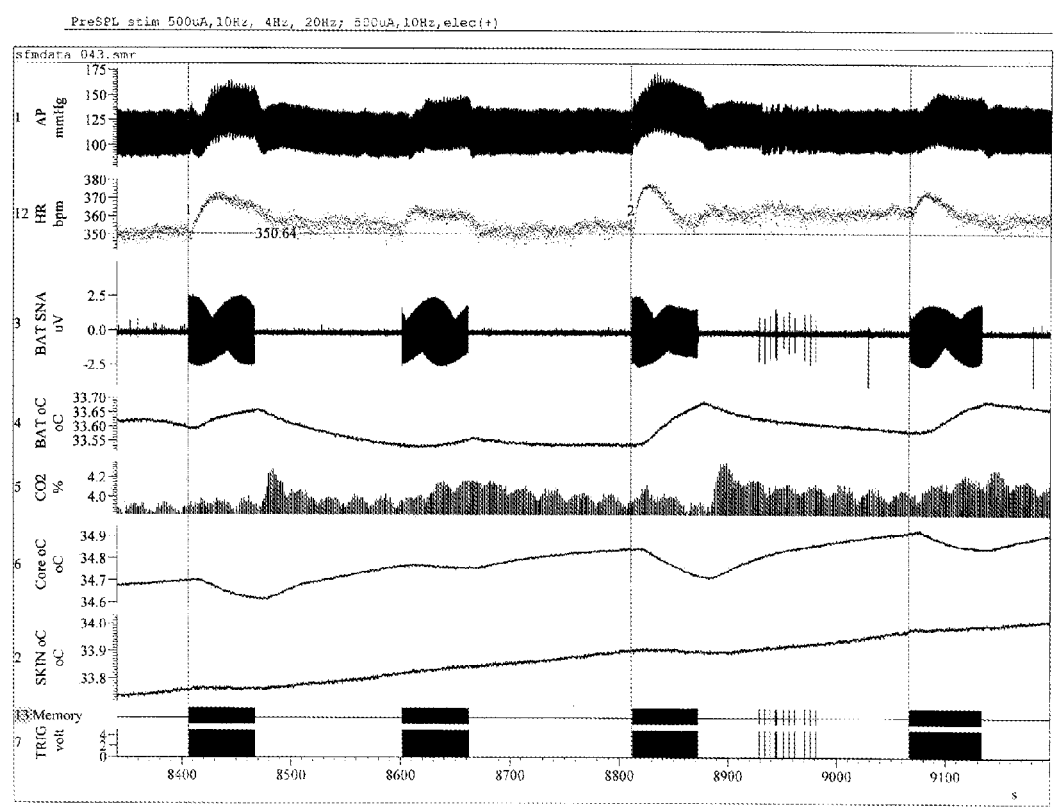
FIG MMM

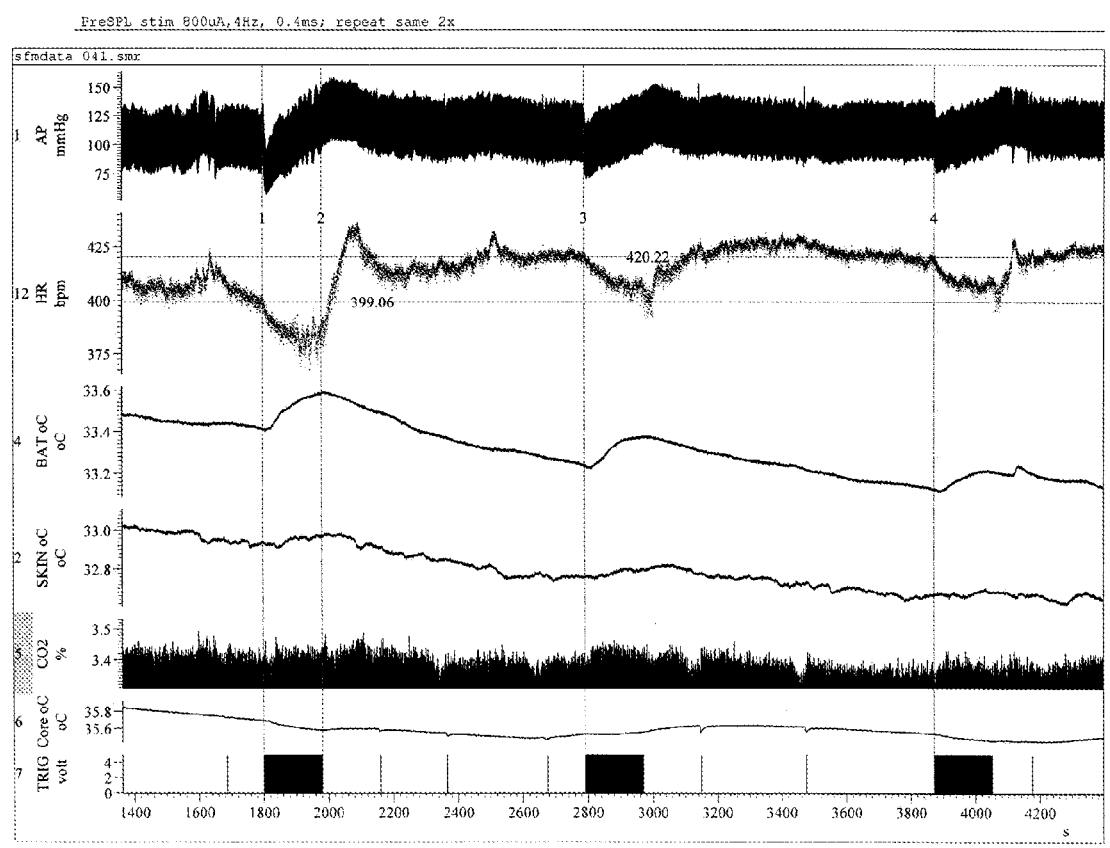
FIG NNN

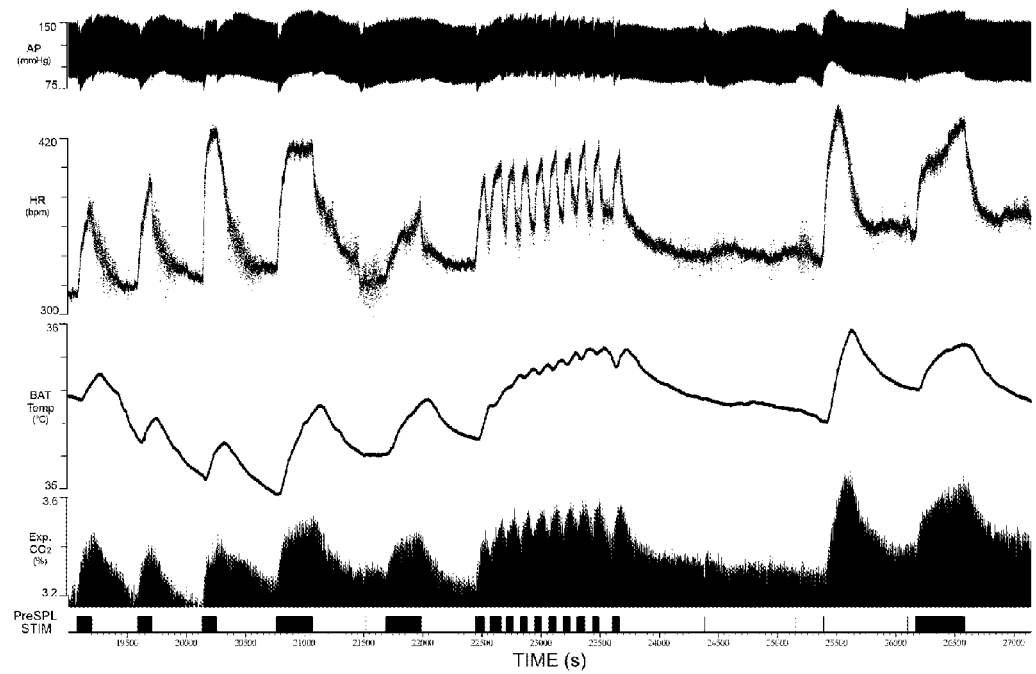
FIG PPP

BROWN ADIPOSE TISSUE UTILIZATION THROUGH NEUROMODULATION

CROSS REFERENCE TO RELATED APPLICATION

This application claims priority from U.S. provisional application 61/176,829, filed May 8, 2009, which is herein incorporated by reference in its entirety.

TECHNICAL FIELD

The present invention is related generally to medical devices and methods. More specifically, the present invention is related to neurostimulation involving brown adipose tissue, for example, neurostimulation of the splanchnic nerves to treat obesity.

BACKGROUND

Obesity

Obesity results from an imbalance between food intake and energy expenditure, such that there is a net increase in fat reserves. Excessive food intake, reduced energy expenditure, or both may contribute to this in balance. Clinically, obesity is defined relative to body mass index (BMI), a measure of body weight to body surface (kg/m2). A normal BMI is considered to be in the range from greater than 30 kg/m2. A BMI in the range from 25-30 is considered overweight, while obese is classified as having a BMI >30. Obesity is classified into 3 subcategories: Class I—moderate; Class II—severe; and Class III very severe.

It is well established that patients with elevated BMIs are at increased risk for a variety of diseases including hypertension and cardiovascular disease, kidney disease, diabetes, dyslipidemia, sleep apnea, and orthopedic problems. Obesity has become pandemic in the U.S. with a prevalence exceeding 30%. The increased demand on health care resources due to obesity and the health problems associated with it are estimated in the U.S. to exceed $200 billion annually.

Appetite and satiety, which control food intake, are partly regulated by the hypothalamus region of the brain. Energy expenditure is also controlled in part by the hypothalamus. The hypothalamus regulates the autonomic nervous system of which there are two branches, the sympathetic and the parasympathetic. The sympathetic nervous system generally prepares the body for action by increasing heart rate, blood pressure, and metabolism. The parasympathetic system prepares the body for rest by lowering heart rate, lowering blood pressure, and stimulating digestion. Destruction of the lateral hypothalamus results in hunger suppression, reduced food intake, weight loss, and increased sympathetic activity. In contrast, destruction of the ventromedial nucleus of the hypothalamus results in suppression of satiety, excessive food intake, weight gain, and decreased sympathetic activity.

The splanchnic nerves carry sympathetic neurons that innervate the organs of digestion and the adrenal glands, while the vagus nerve carries parasympathetic neurons that innervate the digestive system, and as experiments involving hypothalamic destruction have shown, those neurons involved in the feeding and weight gain response.

Experimental and observational evidence suggests that there is a reciprocal relationship between sympathetic nervous system activity and food intake, with an increase in sympathetic activity generally leading to a reduction in food intake. These effects are mediated by specific neuropeptides (e.g., neuropeptide Y, galanin) known to decrease sympathetic activity, which in turn triggers an increase food intake. Other peptides such as cholesystokinin, leptin, and enterostatin, increase sympathetic activity, thus decreasing food intake. Ghrelin is a peptide that is secreted by the stomach and which is associated with hunger. Peak plasma levels of this peptide occur just prior to mealtime, and ghrelin levels are increased after weight loss. Sympathetic activity can suppress ghrelin secretion. PYY is a hormone released from the intestine that also plays a role in satiety. PYY levels increase after meal ingestion. Sympathetic activity can increase PYY levels. Similarly, drugs such as nicotine, ephedrine, caffeine, subitramine, dexfenfluramine, which lead to an increase in sympathetic activity, also reduce food intake.

Appetite is stimulated by various psychosocial factors, but also by low blood glucose levels, as well as mechanical receptors in the gastrointestinal tract. For example, cells in the hypothalamus that are sensitive to glucose levels are thought to play a role in the hunger response, increasing the sensation of hunger as glucose levels decrease. In response, activation of the sympathetic nervous system leads to an increase in plasma glucose levels. Similarly, a feeling of satiety can be promoted by distention of the stomach and delayed gastric emptying. Sympathetic nerve activity reduces gastric and duodenal motility, causes gastric distention, and can increase contraction of the pyloric sphincter, which can result in distention and delayed emptying of the stomach contents.

The sympathetic nervous system also plays a role in energy expenditure and thus the tendency towards obesity. Genetically inherited obesity in rodents is characterized by decreased sympathetic activity in adipose tissue and other peripheral organs. Catecholamines and cortisol, which are released by the sympathetic nervous system, cause a dose-dependent increase in resting energy expenditure. In humans, a negative correlation between body fat and plasma catecholamine levels has been reported.

Over- or under-feeding lean human subjects can have significant effects on sympathetic nervous system activation and energy expenditure. For example, weight loss in obese subjects is associated with a compensatory decrease in energy expenditure, which promotes regaining previously lost weight, a common problem that limits the effectiveness of classic diet and exercise weight loss programs. Conversely, drugs that activate the sympathetic nervous system, such as ephedrine, caffeine, or nicotine, are known to increase energy expenditure. Smokers are known to have lower body fat stores and increased energy expenditure relative to non-smokers. Weight gain is a commonly reported consequence of quitting smoking. The sympathetic nervous system also plays an important role in regulating energy substrates such as fat and carbohydrate. Metabolism of glycogen and fat, needed to support increased energy expenditure, is increased by sympathetic activation.

Animal research shows that acute electrical activation of the splanchnic nerves causes a variety of physiologic changes. Electrical activation of a single splanchnic nerve in dogs and cows causes a frequency dependent increase in catecholamine, dopamine, and cortisol secretion, and circulating plasma levels of these compounds that lead to increased energy expenditure can be achieved. In adrenalectomized pigs, cows, and dogs, acute single splanchnic nerve activation causes increased blood glucose levels with concomitant reduction in liver glycogen stores. In dogs, single splanchnic nerve activation causes increased pyloric sphincter tone and decreased duodenal motility, reducing the rate of food passage through the gastrointestinal tract, and in turn leading to a sensation of satiety. Moreover, sympathetic, and specifically splanchnic nerve, activation can result in suppression of insulin and leptin hormone secretion.

First-line therapy for obesity treatment is typically behavior modification involving reduced food intake and/or increased exercise. However, these approaches frequently fail and behavioral treatment is commonly supplemented by administration of pharmacologic agents known to reduce appetite and/or increase energy expenditure. Commonly used pharmacologic agents include dopamine and a dopamine analogues, acetylcholine and cholinesterase inhibitors. Pharmacologic therapy is typically delivered orally. However, treating obesity with drugs frequently results in undesirable side effects, including systemic effects such as tachycardia, sweating, and hypertension. In addition, tolerance can develop such that the response to the drug is reduced even one higher doses are used.

Brown Adipose Tissue

Brown adipose tissue (BAT) or brown fat is one of the two types of adipose tissue (the other being white adipose tissue) that is present in many newborn or hibernating mammals. Its primary function is to generate body heat. In contrast to white adipocytes (fat cells), which contain a single lipid droplet, brown adipocytes contain numerous smaller droplets and a much higher number of mitochondria. Brown fat also contains more capillaries than white fat, since it has a greater need for oxygen than most tissues.

The mitochondria in a eukaryotic cell utilize fuels to produce energy (in the form of ATP). This process involves storing energy as a proton gradient, also known as the proton motive force (PMF), across the mitochondrial inner membrane. This energy is used to synthesize ATP when the protons flow across the membrane (down their concentration gradient) through the ATP synthase enzyme; this is known as chemiosmosis.

In endothermic animals, body heat is maintained by signaling the mitochondria to allow protons to run back along the gradient without producing ATP. This can occur since an alternative return route for the protons exists through an uncoupling protein in the inner membrane. This protein, known as uncoupling protein 1 (thermogenin), facilitates the return of the protons after they have been actively pumped out of the mitochondria by the electron transport chain. This alternative route for protons uncouples oxidative phosphorylation and the energy in the PMF is released as heat.

To some degree, all cells of endotherms give off heat, especially when body temperature is below a regulatory threshold. However, brown adipose tissue is highly specialized for this non-shivering thermogenesis. First, each cell has a higher number of mitochondria compared to more typical cells. Second, these mitochondria have a higher-than-normal concentration of thermogenin in the inner membrane.

In neonates (newborn infants), brown fat, which then makes up about 5% of the body mass and is located on the back, along the upper half of the spine and toward the shoulders, is of great importance to avoid lethal cold. The burning of brown fat provides a baby with an alternative means of heat regulation.

Until very recently, it was believed that, when growing up, most of the mitochondria (which are responsible for the brown color) in brown adipose tissue disappear, and the tissue becomes similar in function and appearance to white fat—as a mere fat deposit. But more recently it has become clear that brown fat is not closely related to white fat, but to skeletal muscle, instead. Further, recent studies using PET scanning of adult humans have shown that it is still present in adults in the upper chest and neck. The remaining deposits become more visible (increasing tracer uptake) with cold exposure and less visible if an adrenergic beta blocker is given before the scan. See Nedergaard J, Bengtsson T, Cannon B (August 2007). "Unexpected evidence for active brown adipose tissue in adult humans". Am. J. Physiol. Endocrinol. Metab. 293 (2): E444-52, 2006.

Neurostimulation for the treatment of obesity has been discussed by applicants and by others. Optimum stimulation electrode placement is desirable for best results. Increased metabolic rates would also be desirable for best results. What would be desirable are methods for optimizing stimulation electrode placement and weight loss through increased metabolic rate.

SUMMARY

The present invention includes methods for placing an electrode for stimulating a sympathetic nerve for the purpose of inducing weight loss. The method can include determining which of the right and left sides of the human back has the greater amount of brown adipose tissue (BAT), selecting the side having the greater amount of BAT, and preferentially stimulating the side having the greater amount of BAT. Some methods utilize a PET scan to visualize the BAT. The patient temperature may be held at lower than room temperature or lower than 68 degrees F., in order to make the BAT generate heat and reveal itself. Infra red scanning may be used in some embodiments. Subcutaneous temperature electrode may be used to measure BAT temperature in some embodiments. In some methods the electrode is placed along the splanchnic Nerve. In other methods, the electrode is placed along the sympathetic chain.

The present invention also includes methods for placing a chronic electrode on a splanchnic nerve and/or on the sympathetic chain in the thoracic cavity. The method can include stimulating the right side nerve or chain and the left side nerve or chain using a temporary electrode and observing the response of Brown Adipose Tissue (BAT) on the respective sides of the body. The method can then include and preferentially placing the chronic electrode on the side of the body showing the greatest response to stimulation using the temporary electrode.

Methods according to the present invention also include methods for determining a stimulation frequency for stimulating a sympathetic nerve. One such method includes stimulating the nerve at a variety of frequencies while monitoring the response of Brown Adipose Tissue (BAT), and stimulating the nerve at a frequency showing an optimal BAT response to the stimulating. The method can also include determining a frequency corresponding to a high BAT temperature relative to other BAT temperatures at other corresponding frequencies is selected for the stimulating, and stimulating at or neat that determined frequency. Such methods can be used with nerves and/or the sympathetic chain.

One driving circuit for brown adipose tissue comes from nerves that are in deep brain structures. In particular, this can include stimulation of medullary raphe nuclei with standard DBS parameters in order to drive BAT and increase resting energy expenditure. This can include selective stimulation of cells that also block noxious stimuli—so called "OFF" cells.

ON cells are excited by noxious cutaneous stimulation, inhibited by opioids, and facilitate nociceptive transmission, whereas OFF cells are inhibited by noxious cutaneous stimulation, excited by opioids, and suppress nociceptive transmission. OFF cells, are present in greater numbers in the medullary raphe nuclei and have been associated with driving BAT activity. Typically it is non-serotonergic cells that drive BAT activity. Furthermore disinhibition/blocking of RM-RP cells increases BAT nerve activity from almost nothing to continuous, near maximal activity.

Some methods according to the present invention include:
a) stimulating the medullary raphe OFF cells;
b) blocking the raphe palladus cells; or both a and b. This can be facilitated by deep brain stimulation with a number of unique electrodes, or a single programmable electrode array.

Stimulation of deep brain nuclei: May be done via stimulation of the Rostral Raphe pallidus (RPa). The RPa contains potential sympathetic premotor neurons that project to the region of sympathetic preganglionic neurons in the thoracic spinal cord. Disinhibition of neurons in RPa elicit a dramatic increase in BAT SNA, with only a small rise in SPL SNA [which is highly dependent on arterial pressure].

Stimulation of BAT depots: May also be done by placing button electrodes within the BAT or on sympathetic nerves going into BAT depots. The main depots are located along the shoulder area. FDG-PET could be utilized to image the BAT depots in order to select the optimal placement of the device.

Stimulation can mimic the normal ultradian rhythm of BAT i.e. stimulation burst every 1½ hours. Bursts can be delivered in bursts of 3-4 Hz or 6-7 Hz., in some embodiments. Some embodiments use stimulation frequencies that are characteristic of brown-fat sympathetic nerve activity i.e. stimulate with frequencies in the 3-10 Hz range, and/or use the ultradian rhythm with a spike about every 1½ hours to deliver a brief dose of stimulation.

The stimulation electrode embodiment would likely be different depending on the stimulation target i.e. for a RPa stimulation, the electrode could resemble a cylindrical stick with multiple electrodes on the tip; direct activation of the brown fat depot, could involve an electrode that is flatter, providing a large field of activation across an entire 5 mm×5 mm area of brown adipose tissue.

Optimization of therapy involving stimulation of greater splanchnic nerve can be used: E.g. Use a temperature sensor under the skin to measure activation during stimulation; Use a nerve-guidance device with a hook in order to record from sympathetic nerves in BAT; Use FDG PET scans in a cold room to identify metabolically active brown fat; Select the side for implant based on the distribution of brown fat depots and the temperature increases/burst activity measured by the nerves in that area.

This therapy can include modulation of the sympathetic nervous system which innervates brown adipose tissue. In order to optimize delivery of the therapy, it would be helpful to leverage the metabolic characteristics of this tissue in order to "titrate therapy" or implant the most appropriate device configuration. Also, brown adipose fat depots are not uniformly distributed on the right and left side of the body. Stimulating the correct side, so as to maximize the effect of the therapy or detect the optimal side to implant the device would be invaluable for this therapy.

DETAILED DESCRIPTION

Weight control can be viewed in relatively simple terms as the net difference between energy intake and expenditure. Where intake exceeds expenditure an individual will gain weight over time, and conversely where expenditure exceeds intake, net weight loss is realized. The goal in any weight control paradigm is thus finding a way in which to reduce intake and/or increase expenditure in order to create a net caloric deficit. This is the basis of all diet and exercise programs. While conceptually simple, for a variety of reasons, most diet and/or exercise programs are generally ineffective, typically because of the difficulty in maintaining compliance with the diet and/or exercise regime. However, since appetite and energy expenditure are ultimately regulated by the nervous system, it is hypothetically possible to control weight not by voluntary adherence to a diet/exercise program, but rather through direct modulation of components of the nervous system that are involved in appetite and metabolism.

The human nervous system is a complex network of nerve cells, or neurons, found centrally in the brain and spinal cord and peripherally in various nerves of the body. Neurons comprise a cell body, dendrites and an axon. Clusters of neuronal cell bodies are termed ganglia. A nerve is a collection of neurons that are generally organized to serve a particular part of the body. A single nerve may contain several hundred to several hundred thousand neurons. Nerves often contain both afferent and efferent neurons. Afferent neurons carry signals back to the central nervous system (CNS) while efferent neurons carry signals away from the CNS to the periphery. Electrical signals are conducted via neurons and nerves. Neurons release neurotransmitters at synapses (connections) with other nerves to allow continuation and modulation of the electrical signal. In the periphery, synaptic transmission often occurs at ganglia. Nerves can also release transmitters at their termini permitting neuromodulation of target tissues (e.g., adrenal gland).

The electrical signal generated by a neuron is known as an action potential. Action potentials are initiated when a voltage potential across the neuronal cell membrane exceeds a certain threshold, resulting in the opening of ion channels in the neuronal cell membrane. The action potential is then propagated down the length of the neuron. The action potential of a nerve is complex and represents the sum of action potentials of the individual neurons within it.

Neurons can be myelinated, un-myelinated, of large axonal diameter, or small axonal diameter. In general, the speed of action potential conduction increases with myelination and with neuron axonal diameter. Accordingly, neurons are classified into type A, B and C neurons based on myelination, axon diameter, and axon conduction velocity. In terms of axon diameter and conduction velocity, A conduct faster than B, which in turn conduct faster than C neurons.

Figure 1:
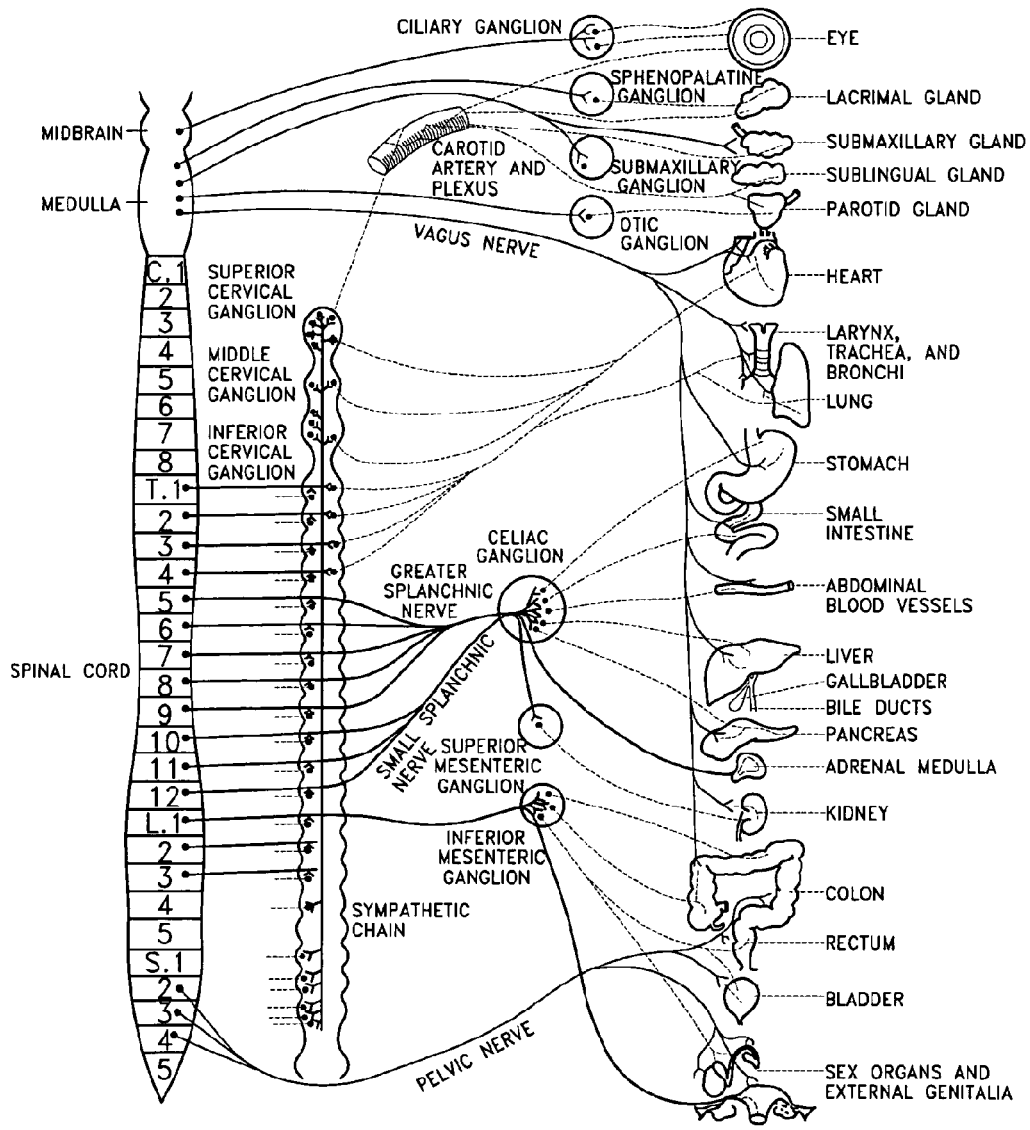
FIG. 1 is a diagram of the efferent autonomic nervous system.

The autonomic nervous system is a subsystem of the human nervous system that controls involuntary actions of the smooth muscles (blood vessels and digestive system), the heart, and glands, as shown in FIG. 1. The autonomic nervous system is divided into the sympathetic and parasympathetic systems. The sympathetic nervous system generally prepares the body for action by increasing heart rate, increasing blood pressure, and increasing metabolism. The parasympathetic system prepares the body for rest by lowering heart rate, lowering blood pressure, and stimulating digestion.

Figure 2:
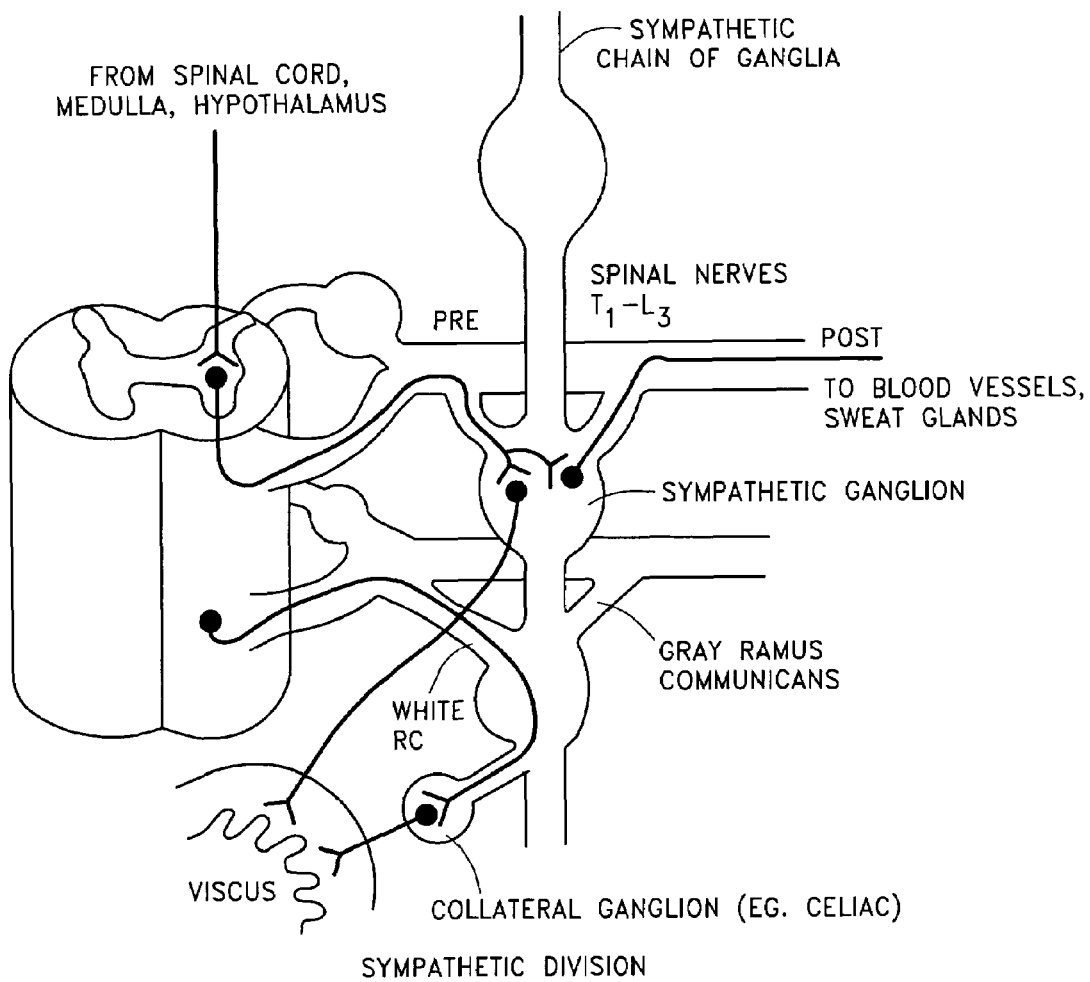
FIG. 2 is a diagram of the sympathetic nervous system.

The hypothalamus controls the sympathetic nervous system via descending neurons in the ventral horn of the spinal cord, as shown in FIG. 2. These neurons synapse with preganglionic sympathetic neurons that exit the spinal cord and form the white communicating ramus. The preganglionic neuron can either synapse in the paraspinous ganglia chain or pass through these ganglia and synapse in a peripheral, or collateral, ganglion such as the celiac or mesenteric. After synapsing in a particular ganglion, a postsynaptic neuron continues on to innervate the organs of the body (heart, intestines, liver, pancreas, etc.) or to innervate the adipose tissue and glands of the periphery and skin. Preganglionic neurons of the sympathetic system are typically myelinated type A and B neurons, while postganglionic neurons are typically unmyelinated type C neurons.

Mechano receptors and chemoreceptors in the gut often transmit their sensory information using frequency encoding, typically over A and B type fibers. The distended gut can distend the stretch receptors which generate a higher frequency signal when stretched compared to when they are not stretched, in one example. Nutrient receptors in the gut can generate different frequency signals in the presence of a specific nutrient, in another example. These frequency encoded signals travel afferently to the brain, and can indicate fullness and/or the presence of nutrients.

Figure 3:
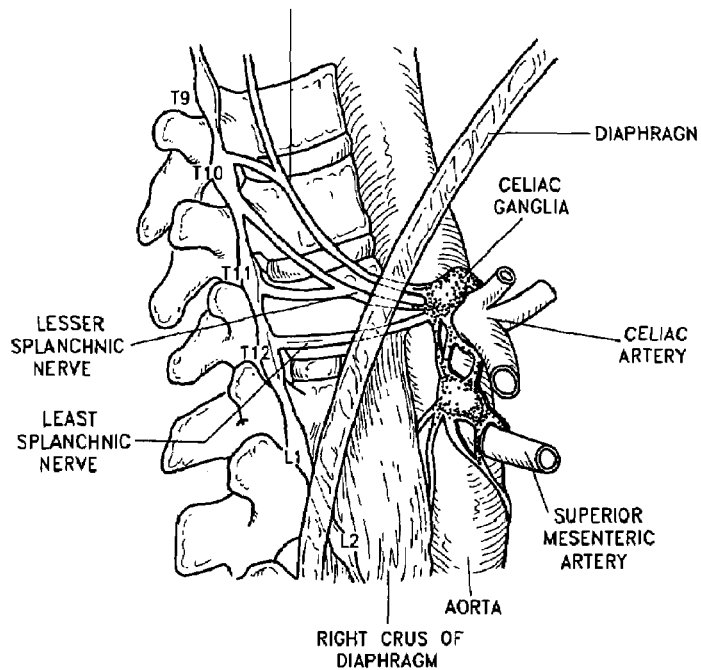
FIG. 3 is an elevation view of the splanchnic nerves and celiac ganglia.

Several large sympathetic nerves and ganglia are formed by the neurons of the sympathetic nervous system, as shown in FIG. 3. The greater splanchnic nerve (GSN) is formed by efferent sympathetic neurons exiting the spinal cord from thoracic vertebral segment numbers 4 or 5 (T4 or T5) through thoracic vertebral segment numbers 9 or 10 or 11 (T9, T10, or T11). The lesser splanchnic (lesser SN) nerve is formed by preganglionic sympathetic efferent fibers from T10 to T12 and the least splanchnic nerve (least SN) is formed by fibers from T12. The GSN is typically present bilaterally in animals, including humans, with the other splanchnic nerves having a more variable pattern, being present unilaterally, bilaterally and sometimes even absent.

The splanchnic nerves run along the anterior-lateral aspect of the vertebral bodies and pass out of the thorax entering the abdomen through the crus of the diaphragm. The nerves run in proximity to the azygous veins. Once in the abdomen, neurons of the GSN synapse with postganglionic neurons primarily in celiac ganglia. Some neurons of the GSN pass through the celiac ganglia and synapse on in the adrenal medulla. Neurons of the lesser SN and least SN synapse with postganglionic neurons in the mesenteric ganglia.

Postganglionic neurons, arising from the celiac ganglia that synapse with the GSN, innervate primarily the upper digestive system, including the stomach, pylorus, duodenum, pancreas, and liver. In addition, blood vessels and adipose tissue of the abdomen are innervated by neurons arising from the celiac ganglia/greater splanchnic nerve. Postganglionic neurons of the mesenteric ganglia, supplied by preganglionic neurons of the lesser and least splanchnic nerve, innervate primarily the lower intestine, colon, rectum, kidneys, bladder, and sexual organs, and the blood vessels that supply these organs and tissues.

In the treatment of obesity, one embodiment involves electrical activation of the greater splanchnic nerve of the sympathetic nervous system. In some embodiments unilateral activation can be used, although bilateral activation can also be used. The celiac ganglia can also be activated, as well as the sympathetic chain or ventral spinal roots.

Electrical nerve modulation (nerve activation or inhibition) can be accomplished by applying an energy signal (pulse), at a certain frequency, amplitude, and current, to the neurons of a nerve (nerve stimulation). Where the energy pulse exceeds the activation threshold for neurons in the nerve, those neurons will depolarize, resulting in the production of action potentials. The cumulative action potential for the nerve will depend on the extent of recruitment of individual neurons within the nerve (i.e., the number of neurons who are provoked to depolarize). The amount of energy applied is a function of the current amplitude and pulse width duration. Activation or inhibition can be a function of the frequency, with low frequencies on the order of 1 to 50 Hz resulting in activation, and high frequencies greater than 100 Hz generally resulting in inhibition Inhibition can also be accomplished by continuous energy delivery resulting in sustained depolarization, which leads to neuronal accommodation (desensitization). Different neuronal types may respond to different frequencies and energies with activation or inhibition.

Each neuronal type (A, B, or C neurons) has a characteristic pulse amplitude-duration profile (energy pulse signal) that leads to activation. Myelinated neurons (types A and B) can generally be stimulated with relatively low current amplitudes on the order of 0.1 to 5.0 milliamperes, and short pulse widths on the order of 50 to 200 microseconds. Unmyelinated type C fibers typically require longer pulse widths, on the order of 300 to 1,000 microseconds, and higher current amplitudes. This difference in energy for activation can be advantageously exploited in order to selectively stimulate certain subsets of neurons in a nerve containing mixed neuronal types. This is of particular use in modulating nerves such as the splanchnic, as the splanchnic nerves contains both afferent pain neurons, which are typically type C neurons, and efferent preganglionic neurons, which are myelinated type B neurons. Thus, in a therapy such as obesity treatment involving splanchnic nerve activation, it is desirable to activate the efferent type B neurons and not the afferent type C pain neurons. This can be effectively accomplished by varying the energy pulse signal.

A fibers are an integral part of the afferent stimulation and signaling. The A fibers can be activated at relatively low stimulation intensity and are often activated in early, lower current portions of some therapies and doses according to the present invention.

Two important parameters related to stimulation of peripheral nerves of mixed neuronal type are the rheobase and chronaxie. These two parameters are a function of the stimulus duration and stimulus strength (current amplitude). The rheobase is the lower limit of the stimulus strength below which an action potential cannot be generated, regardless of the stimulus duration. The chronaxie is the stimulus duration corresponding to twice the rheobase. This is a measure of excitability of the mixed peripheral nerve. It is generally not desirable to stimulate a peripheral nerve at stimulus intensities greater than the chronaxie. The chronaxie of the splanchnic nerve is estimated to be between approximately 150 microseconds and 400 microseconds.

Figure 4:
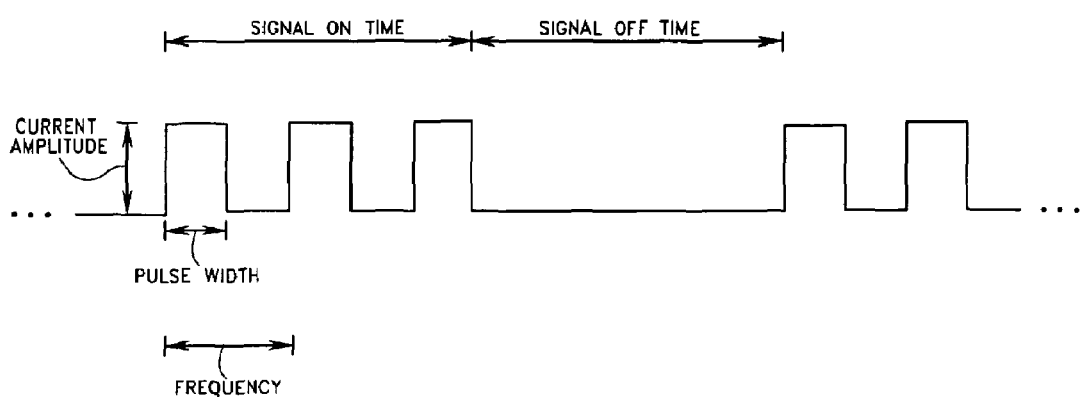
FIG. 4 is a schematic of an exemplary prior art stimulation pattern which can be used in the present method of the invention.

Various stimulation patterns, ranging from continuous to intermittent, can be utilized. With intermittent stimulation, energy is delivered for a period of time at a certain frequency during the signal-on time as shown in FIG. 4. The signal-on time is followed by a period of time with no energy delivery, referred to as signal-off time.

Superimposed on the stimulation pattern are the parameters of pulse frequency and pulse duration. The treatment frequency may be continuous or delivered at various time periods within a day or week. The treatment duration may last for as little as a few minutes to as long as several hours.

Pulse generation for electrical nerve modulation can be accomplished using a pulse generator. Pulse generators can use conventional microprocessors and other standard electrical components. A pulse generator for this embodiment can generate a pulse, or energy signal, at frequencies ranging from approximately 0 Hz (i.e., constant current) to 300 Hz, a pulse width from approximately 10 to 1,000 microseconds, and a constant current of between approximately 0.1 milliamperes to 20 milliamperes. The pulse generator can be capable of producing a ramped, or sloped, rise in the current amplitude and/or frequency. In some embodiments, a pulse generator can communicate with an external programmer and/or monitor. Passwords, handshakes and parity checks can be employed for data integrity. The pulse generator can be battery operated or operated by an external radiofrequency device. Because the pulse generator, associated components, and battery may be implanted they are preferably encased in an epoxy-titanium shell.

Figure 5:
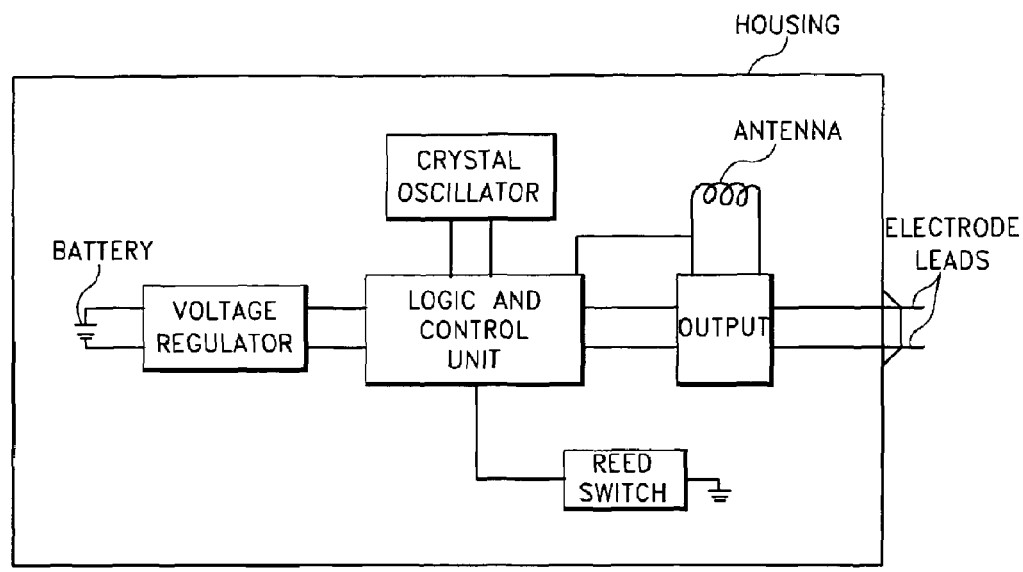
FIG. 5 is schematic of an exemplary prior art pulse generator which can be used in the method of the present invention.

A schematic of an implantable pulse generator (IPG) is shown in FIG. 5. Components can be housed in the epoxy-titanium shell. A battery supplies power to the logic and control unit. A voltage regulator controls the battery output. A logic and control unit can control the stimulus output and allow for programming of the various parameters such as pulse width, amplitude, and frequency. In addition, stimulation pattern and treatment parameters can be programmed at the logic and control unit. A crystal oscillator provides timing signals for the pulse and for the logic and control unit. An antenna is used for receiving communications from an external programmer and for status checking the device. An output section couples to the electrodes and leads that carry the energy pulse to the nerve. A reed switch allows manual activation using an external magnet. Devices powered by an external radiofrequency device can be used to limit the components to primarily a receiving coil or antenna.

The IPG can be coupled to a lead and electrode assembly. The lead can comprise a bundle of electrically conducting wires insulated from the surroundings by a non-electrically conducting coating. Where used, wires of the lead connect the IPG to the stimulation electrodes, which transfers the energy pulse to the nerve. A single wire may connect the IPG to the electrode, or a wire bundle may connect the IPG to the electrode. Wire bundles may or may not be braided. Wire bundles are preferred because they increase reliability and durability. Alternatively, a helical wire assembly could be utilized to improve durability with flexion and extension of the lead. In some embodiments, power could be transmitted from the pulse generator to an end effector electrode wirelessly.

Figure 6:
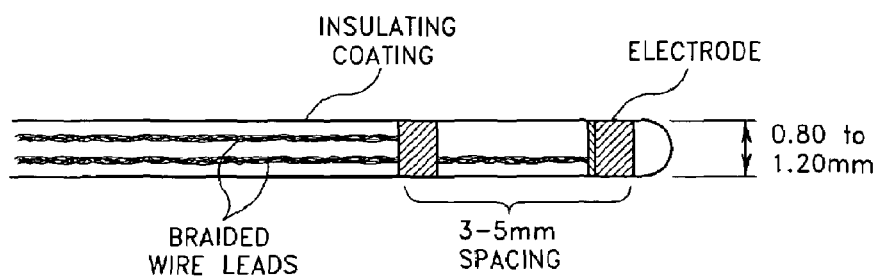
FIG. 6 depicts an exemplary prior art catheter-type lead and electrode assembly which can be used in the method of the present invention.

The electrodes can comprise platinum or platinum-iridium ribbons or rings as shown in FIG. 6. The electrodes are capable of electrically coupling with the surrounding tissue and nerve. The electrodes may encircle a catheter-like lead assembly. The distal electrode may form a rounded cap at the end to create a bullet nose shape. Ideally, this electrode serves as the cathode. A lead of this type may contain 2 to 4 ring electrodes spaced anywhere from 2.0 to 5.0 mm apart with each ring electrode being approximately 1.0 to 10.0 mm in width. Catheter lead electrode assemblies may have an outer diameter of 0.5 mm to 1.5 mm to facilitate percutaneous placement using an introducer.

Bipolar stimulation of a nerve can be accomplished with multiple electrode assemblies with one electrode serving as the positive node and the other serving as a negative node. In this manner nerve activation can be directed primarily in one direction (unilaterally), for example, to selectively activate efferent nerve fibers. Alternatively, a nerve cuff electrode can be employed. Helical cuff electrodes, such as those described in U.S. Pat. No. 5,251,634 (Weinberg), can be used. Cuff assemblies can similarly have multiple electrodes and direct and cause unilateral nerve activation.

Unipolar stimulation can also be performed. As used herein, unipolar stimulation means using only a single electrode on the lead, while the metallic shell of the IPG, or another external portion of the IPG, essentially functions as a second electrode, remote from the first electrode. In some embodiments, unipolar stimulation may be more suitable for splanchnic nerve stimulation than the bipolar stimulation method, particularly if the electrode is to be placed percutaneously under fluoroscopic visualization. With fluoroscopically observed percutaneous placement, it may not always be possible to place the electrodes immediately adjacent the nerve, which is often required for bipolar stimulation.

With unipolar stimulation, a larger energy field is created in order to electrically couple the electrode on the lead with the remote external portion of the IPG, and the generation of this larger energy field can result in activation of the nerve even in the absence of close proximity between the single lead electrode and the nerve. This allows successful nerve stimulation with the single electrode placed only in "general proximity" of the nerve. This allows for significantly greater separation between the electrode and the nerve than the "close proximity" required for effective bipolar stimulation. The magnitude of the allowable separation between the electrode and the nerve will necessarily depend upon the actual magnitude of the energy field that the stimulator generates with the lead electrode in order to couple with the remote electrode. Patch electrodes, cuff electrodes, and transvascular/intravascular electrodes may be used in various embodiments.

In multiple electrode assemblies, some of the electrodes may be used for sensing nerve activity. This sensed nerve activity could serve as a signal to commence stimulation therapy. For example, afferent action potentials in the splanchnic nerve, created due to the commencement of feeding, could be sensed and used to activate the IPG to begin stimulation of the efferent neurons of the splanchnic nerve. Appropriate circuitry and logic for receiving and filtering the sensed signal would be required in the IPG. Thus, in some embodiments, electrodes within the assembly can be used to provide the sensor functionality as described herein with respect to detecting swallowing or some other physiological parameter associated with eating as has been described above.

Because branches of the splanchnic nerve directly innervate the adrenal medulla, electrical activation of the splanchnic nerve results in the release of catecholamines (epinephrine and norepinephrine) into the blood stream. In addition, dopamine and cortisol, which also raise energy expenditure, can be released. Catecholamines can increase energy expenditure by 15% to 20%. By comparison, subitramine, a pharmacologic agent used to treat obesity, increases energy expenditure by only 3% to 5%.

Figure 7:
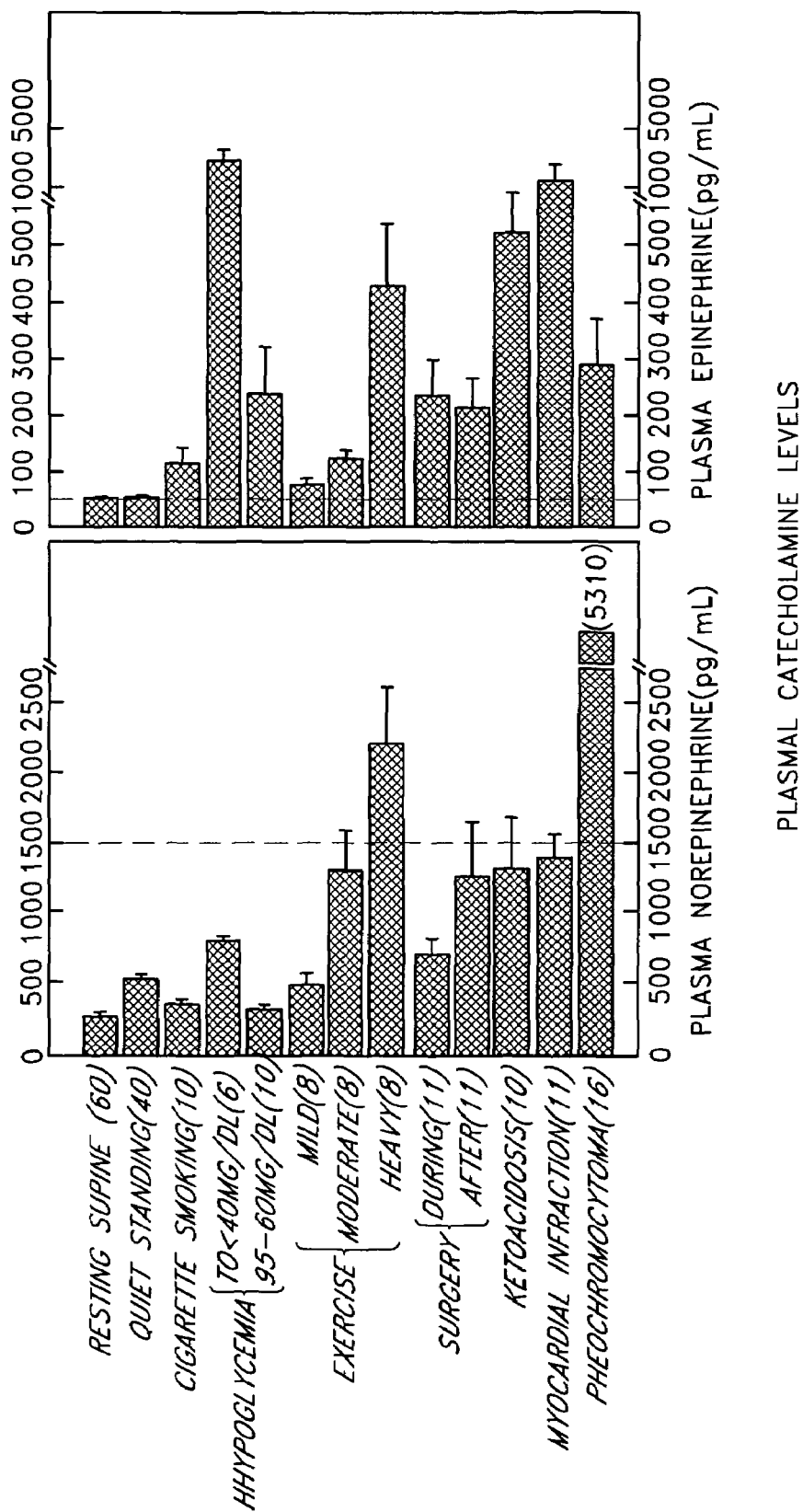
FIG. 7 is a graph of known plasma catecholamine levels in response to various physiologic and pathologic states.

Human resting venous blood levels of norepinephrine and epinephrine are approximately 300 picograms (pg)/milliliter (ml) and 25 pg/ml, respectively, as shown in FIG. 7. Detectable physiologic changes such as increased heart rate occur at norepinephrine levels of approximately 1,500 pg/ml and epinephrine levels of approximately 50 pg/ml. Venous blood levels of norepinephrine can reach as high 2,000 pg/ml during heavy exercise, and levels of epinephrine can reach as high as 400 to 600 pg/ml during heavy exercise. Mild exercise produces norepinephrine and epinephrine levels of approximately 500 pg/ml and 100 pg/ml, respectively. It may be desirable to maintain catecholamine levels somewhere between mild and heavy exercise during electrical sympathetic activation treatment for obesity.

Figure 8A:
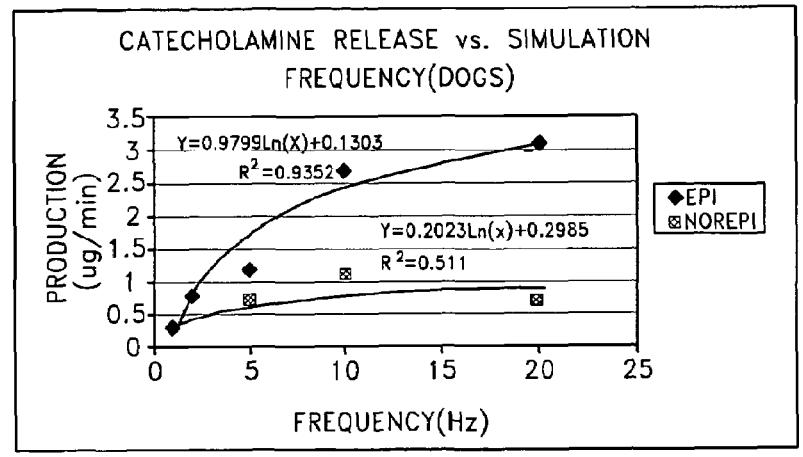
FIGS. 8A, 8B, and 8C are exemplary graphs of the effect of splanchnic nerve stimulation on catecholamine release rates, epinephrine levels, and energy expenditure, respectively.
Figure 8B:
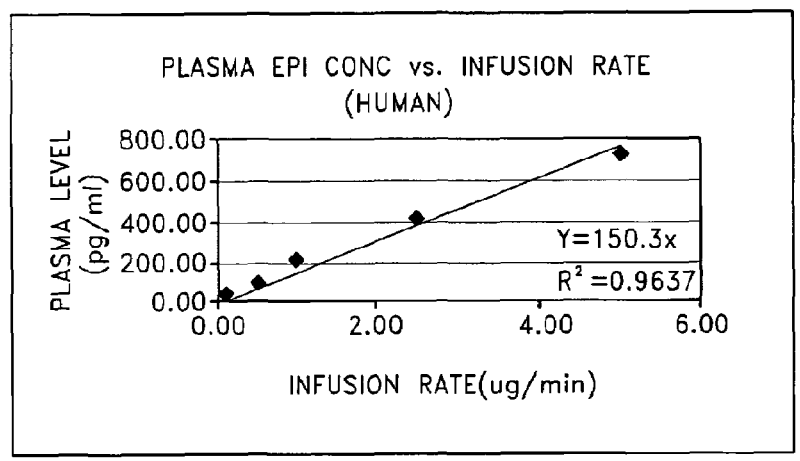
Figure 8C:
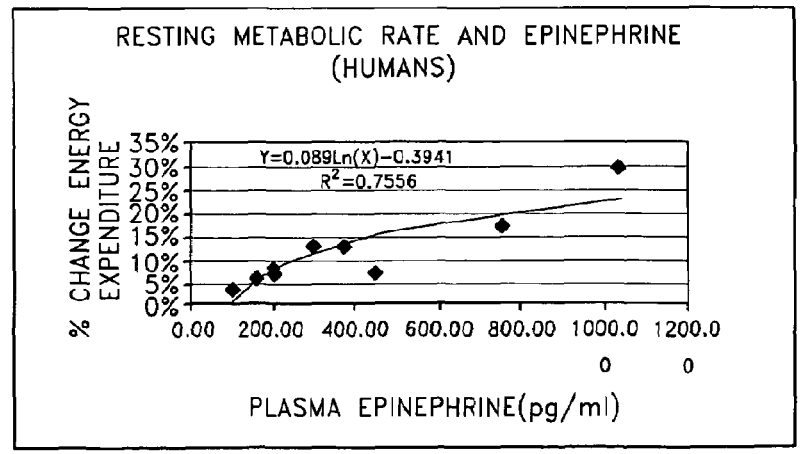

In anesthetized animals, electrical stimulation of the splanchnic nerve has shown to raise blood catecholamine levels in a frequency dependent manner in the range of 1 Hz to 20 Hz, such that rates of catecholamine release/production of 0.3 to 4.0 mug/min can be achieved. These rates are sufficient to raise plasma concentrations of epinephrine to as high as 400 to 600 pg/ml, which in turn can result in increased energy expenditure ranging from 10% to 20% as shown in FIG. 8. During stimulation, the ratio of epinephrine to norepinephrine is 65% to 35%. It may be possible to change the ratio by stimulating at higher frequencies. This may be desired to alter the energy expenditure and/or prevent a rise in MAP.

Energy expenditure in humans ranges from approximately 1.5 kcal/min to 2.5 kcal/min. A 15% increase in this energy expenditure in a person with an expenditure of 2.0 kcal/min would increase energy expenditure by 0.3 kcal/min. Depending on treatment parameters, this could result in an additional 100 to 250 kcal of daily expenditure and 36,000 to 91,000 kcal of yearly expenditure. One pound of fat is approximately 3500 kcal, yielding an annual weight loss of 10 to 26 pounds.

Increased energy expenditure is typically fueled by fat and carbohydrate metabolism, and in extreme cases of weight loss by metabolism of protein. Postganglionic branches of the splanchnic nerve innervate the liver and fat deposits of the abdomen. Activation of the splanchnic nerve can result in fat metabolism and the liberation of fatty acids, as well as glycogen breakdown and the release of glucose from the liver. Fat metabolism coupled with increased energy expenditure may result in a net reduction in fat reserves.

Figure 9:
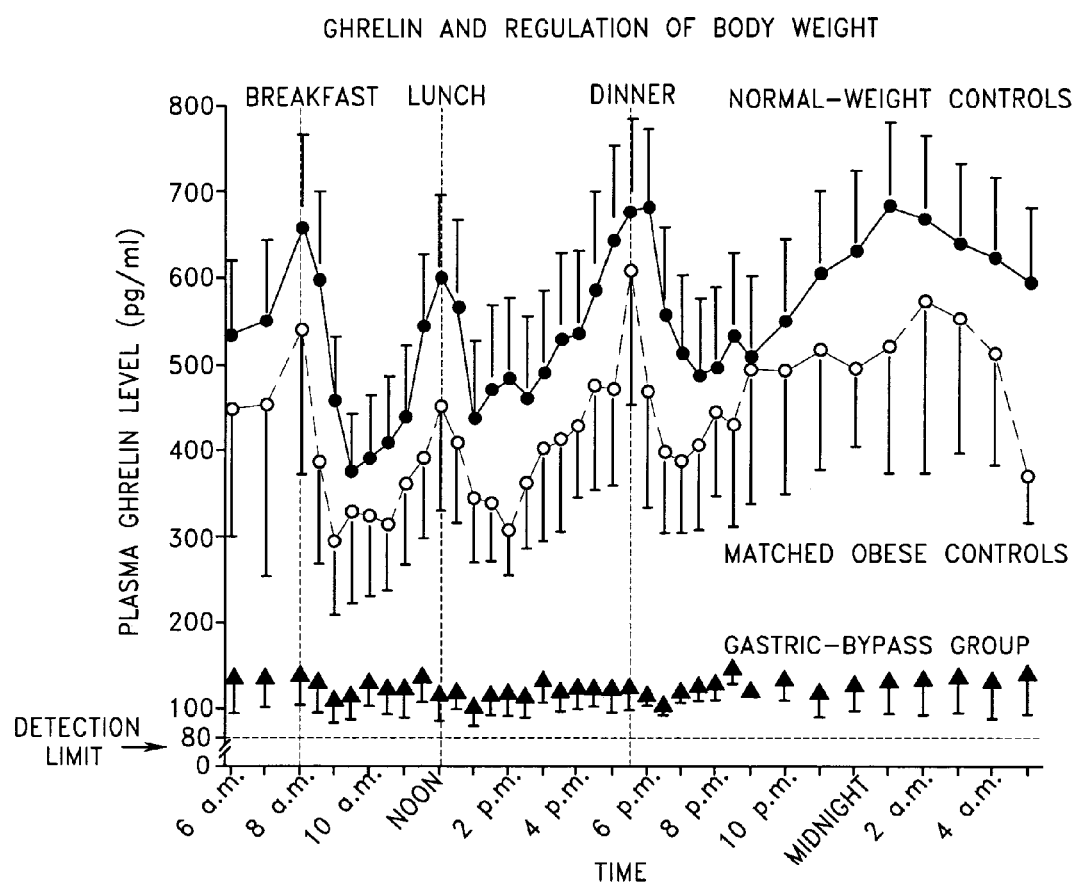
FIG. 9 is a graph of known plasma ghrelin level over a daily cycle.

It may also be desirable to titrate obesity therapy to plasma ghrelin levels. In humans, venous blood ghrelin levels range from approximately 250 pg/ml to greater than 700 pg/ml as shown in FIG. 9. Ghrelin levels rise and fall during the day with peak levels typically occurring just before meals. In patients with gastric bypass surgery, an effective treatment for obesity, ghrelin levels are more static and typically stay in a low range of 100 to 200 pg/ml. Splanchnic nerve activation, in the treatment of obesity, could be titrated to keep ghrelin levels in the low range below 250 to 300 pg/ml. Reductions in food intake comparable to the increases in energy expenditure (i.e., 100 to 250 kcal/day), could yield a total daily kcal reduction of 200 to 500 per day, and 20 to 50 pounds of weight loss per year.

In anesthetized animals, electrical activation of the splanchnic nerve has also been shown to decrease insulin secretion. In obesity, insulin levels are often elevated, and insulin resistant diabetes (Type II) is common Down-regulation of insulin secretion by splanchnic nerve activation may help correct insulin resistant diabetes.

Alternatively, in some embodiments, an alpha-sympathetic receptor blocker, such a prazosin could be used to blunt the rise in MAP. Alpha-blockers are commonly available antihypertensive medications. The rise in MAP seen with splanchnic nerve stimulation is the result of alpha-receptor activation, which mediates arterial constriction. Because the affects of this therapy on reduced food intake and energy expenditure are related to beta-sympathetic receptor activity, addition of the alpha-blocker would not likely alter the therapeutic weight loss benefits. Given the potential for relatively short period of stimulation with the present method, however, it may be possible to avoid altogether the increase in MAP that attends other stimulatory programs, an additional advantage provided by the present invention.

Figure 10:
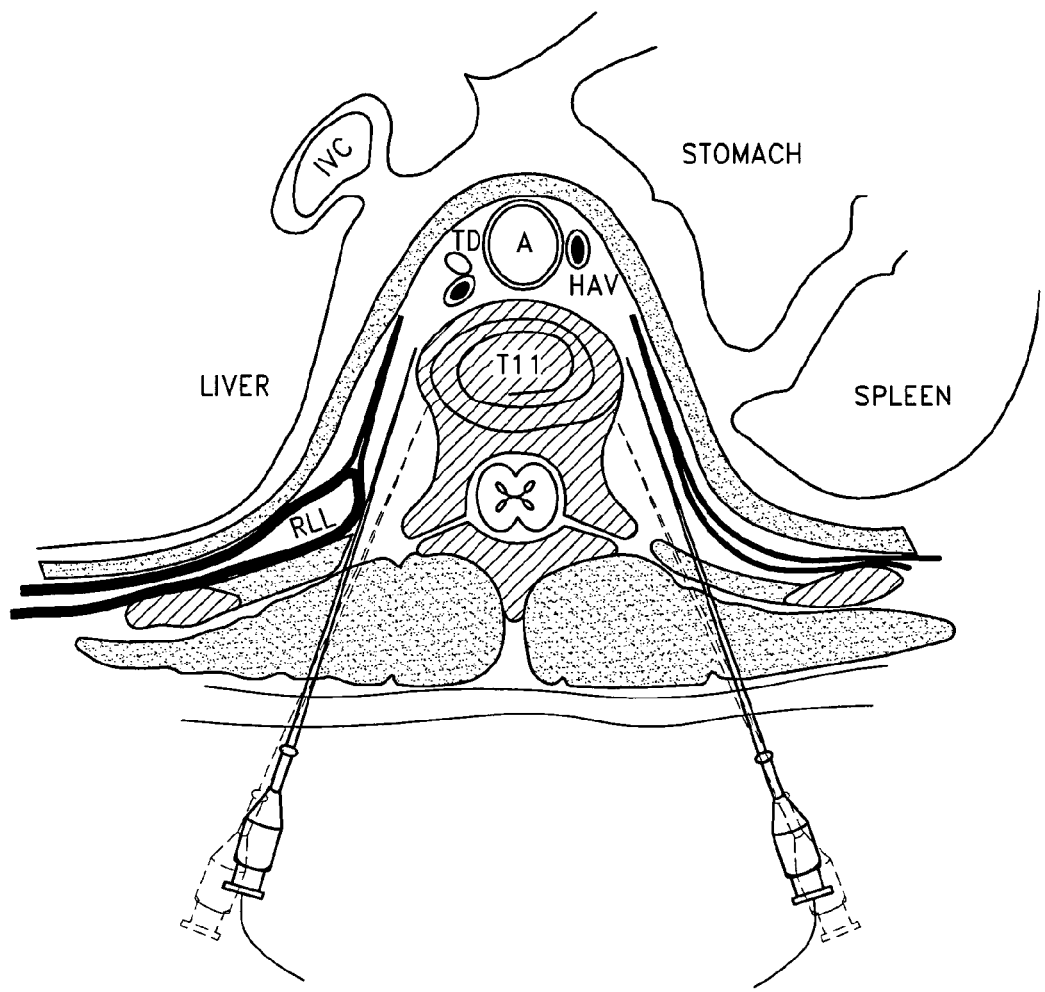
FIG. 10 is a section view of an exemplary instrument placement which can be used in the method of the present invention for implantation of an electrode assembly;
FIGS DD1A and DD1B illustrate a first dosing pattern that can be delivered in some embodiment methods, having an intensity ramp and substantially constant frequency over the dose length.
FIG DD2 is a bar chart having an experimental result from canines showing rises in biomarkers using four variations in stimulation.
FIG DD3 is a bar chart having an experimental result from canines showing repeatable rises in biomarkers over a series of three doses.
FIGS DD4 and DD5 are current and frequency plots for a second dosing algorithm.
FIGS DD6 and DD7 are current and frequency plots for a third dosing algorithm.
FIG XXX is an illustration of the BAT deposit location in a normal human male.
FIG YYY is a FDG PET scan of BAT tissue showing BAT activation at cold temperatures.
FIG ZZZ is a scan showing BAT tissue location in the neck and shoulder area.
FIG MMM is an experimental result plot of stimulating a rat GSN resulting in increased BAT metabolism at varying frequencies.
FIG NNN is another experimental result plot of stimulating a rat GSN resulting in increased BAT metabolism at varying frequencies.
FIG PPP is another experimental result plot of stimulating a rat GSN resulting in increased BAT metabolism at varying frequencies.

Implantation of the lead/electrode assembly for activation of the greater splanchnic nerve can ideally be accomplished percutaneously using an introducer as shown in FIG. 10. The introducer can be a hollow needle-like device that would be placed posteriorly through the skin between the ribs paramidline at the T9-T12 level of the thoracic spinal column. A posterior placement with the patient prone is preferred to allow bilateral electrode placement at the splanchnic nerves, if required. Placement of the needle could be guided using fluoroscopy, ultrasound, or CT scanning Proximity to the splanchnic nerve by the introducer could be sensed by providing energy pulses to the introducer to electrically activate the nerve while monitoring for a rise in MAP. All but the very tip of the introducer would be electrically isolated so as to focus the energy delivered to the tip of the introducer. The lower the current amplitude required to cause a rise in the MAP, the closer the introducer tip would be to the nerve. Ideally, the introducer tip serves as the cathode for stimulation.

Percutaneous placement of the lead electrode assembly could be enhanced using direct or video assisted visualization. An optical port could be incorporated into the introducer. A separate channel would allow the electrode lead assembly to be inserted and positioned, once the nerve was visualized. Alternatively, a percutaneous endoscope could be inserted into the chest cavity for viewing advancement of the introducer to the nerve. The parietal lung pleuron is relatively clear, and the nerves and introducer can be seen running along the vertebral bodies. With the patient prone, the lungs are pulled forward by gravity creating a space for the endoscope and for viewing. This may avoid the need for single lung ventilation. If necessary, one lung could be collapsed to provide space for viewing. This is a common and safe procedure performed using a bifurcated endotracheal tube. The endoscope could also be placed laterally, and positive CO2 pressure could be used to push down the diaphragm, thereby creating a space for viewing and avoiding lung collapse.

Alternatively, stimulation electrodes could be placed along the sympathetic chain ganglia from approximately vertebra T4 to T11. This implantation could be accomplished in a similar percutaneous manner as above. This would create a more general activation of the sympathetic nervous system, though it would include activation of the neurons that comprise the splanchnic nerves.

Alternatively, the lead/electrode assembly could be placed intra-abdominally on the portion of the splanchnic nerve that resides retroperitoneally on the abdominal aorta just prior to synapsing in the celiac ganglia. Access to the nerve in this region could be accomplished laparoscopically, using typical laparoscopic techniques, or via open laparotomy. A cuff electrode could be used to encircle the nerve unilaterally or bilaterally. The lead could be anchored to the crus of the diaphragm. A cuff or patch electrode could also be attached to the celiac ganglia unilaterally or bilaterally. Similar activation of the splanchnic branches of the sympathetic nervous system would occur as implanting the lead electrode assembly in the thoracic region.

An alternative lead/electrode placement can be via a transvascular approach. Due to the proximity of the splanchnic nerves to the azygous veins shown in FIG. 10, and in particular the right splanchnic nerve and right azygous vein, modulation could be accomplished by positioning a lead/electrode assembly in this vessel. The venous system and azygous vein can be accessed via the subclavian vein using standard techniques. The electrode/lead assembly can be mounted on a catheter. A guidewire can be used to position the catheter in the azygous vein. The lead/electrode assembly would include an expandable member, such as a stent. The electrodes can be attached to the stent, and using balloon dilation of the expandable member, can be pressed against the vessel wall so that energy delivery can be transferred to the nerve. An expandable member would allow fixation of the electrode lead assembly in the vessel. The IPG and remaining lead outside of the vasculature can be implanted subcutaneously in a manner similar to a heart pacemaker.

Various doses can be delivered in response to the detection of eating. Three different dosing strategies are described below. Individual or multiple doses from these strategies may be utilized as part of various embodiments of the present invention.

FIGS DD1A and DD1B illustrate one algorithm according to the present invention. In this algorithm, labeled as "Algorithm A" in the figure, the series of doses are delivered in a diurnal pattern, are delivered during typical waking hours, and are not delivered in the typical sleeping hours. In this example, the doses are delivered about 12 times per day. The doses are about a half hour long, with an inter-dose no (or substantially reduced intensity) stimulation period of about one hour in between. Algorithm A, in this example, has a substantially constant frequency, of about 20 Hz. The stimulation intensity ramps up at the beginning of the dose, ramps down at the end of the dose, and has a substantially constant intensity plateau portion in between the up ramp and down ramp.

The intensity is shown as a percent of Maximum Tolerable Current (MTC), a measure of tolerable stimulation intensity. MTC can be measured in various ways, depending on the embodiment. In one embodiment, the patient is stimulated at various intensities and asked which intensity is the maximum they could tolerate after leaving the session. In another method, which can be used in animals and humans, the blood pressure is observed during stimulation and compared to a blood pressure base line the day before the stimulation. The Mean Arterial Pressure (MAP) may be used, which may be approximated as ⅓ times the systolic plus ⅔ times of the diastolic, to give each a proper weighting. A MTC in this embodiment may be the intensity at which MAP increases 20 percent above the baseline.

In one embodiment, the pulse width is held at about ½ ms (500 usec) while the current is varied. In another embodiment, the current is held constant while the pulse width is varied. In still other embodiments, both current and pulse width are varied to vary the pulse width*current product, which is the intensity, having units of time*current which is charge, typically mSec*mA. In some embodiments the MTC has a pulse width of about ½ msec (512 usec in one embodiment) and a current of about 1, 2, or even 3 mA.

In FIGS DD1A and DD1B, the current increases in a ramp over the first 10 minutes, holds constant for 15 minutes, and decreases over the next 5 minutes. This is followed by 60 minutes of no stimulation, followed by another dose, during typical waking hours. In the embodiment illustrated, the first dose occurs at 4:00 and the last dose stops at about 21:00. In this embodiment, the first dose occurs in pre-waking hours. In some embodiments, the first dose does not occur until the patient is normally awake, and the last dose ends at least about one, two, or three hours before sleep is expected, in various embodiments.

Algorithm A thus has a dose time of at least about 15 minutes and less than about 60 minutes, or at least about 20 minutes and less than 40 minutes, or between about 20 and 30 minutes, or about a half hour. The inter dose interval can last at least about one half hour and less than about 3 hours, or at least about ¾ hour and less than about 2 hours, or at least about one hour and less than about two hours, and combinations thereof. The dose can act to increase metabolism for a period sufficient to initiate this sensation and metabolic rate increase, but not so long as to significantly reduce the same effects later, when the dose is repeated again. The dose length can be such that there is no short term degradation in the response. The dose length can be such that there is no decrease in an otherwise increasing biomarker, for example, Free Fatty Acids (FFA), Glucagon, Glycerol, and Glucose, during the dose. This can be explicitly measured on a per patient basis or based on the expected response for a patient, based on other patient responses. In this way, the same dose delivered again during the day can have the same effective result, rather than a blunted response as previous excessive stimulation has caused an accommodation response by the body. The diurnal, lack of stimulation during sleeping hours may also aid in the anti-accommodation performance of the therapy. In this way, the same dose delivered a day later will have substantially the same physiological response as the dose the previous day.

FIG DD2 illustrates the beneficial effect of even short stimulation doses (of 5-7 minutes) followed by about a half hour of off-time. The increases in Free Fatty Acids (FFA), Glucagon, Glycerol, and Glucose (GLU) are all seen.

FIG DD3 illustrates the beneficial effect of a 30 minute dose having a 60 minute inter-dose interval in between. This stimulation used a 60 second on/60 second off duty cycle, at 2 mA and 20 Hz. The change in glycerol and FFA both at 10 minutes after the start of the dose are seen to be significant.

The liberation of FFA and glycerol, indicative of lipolysis, is seen to repeat in doses 2 and 3. This indicates there is some recovery and lack of significant accommodation to the repeated doses. There may well be beneficial effects in addition to the burning of fat stores. The circulating FFA and glucose which result from the dose may well reduce appetite as well, as glucose is added to the blood stream and sensed, for example, by the brain. This can thereby reduce hunger and blunt appetite, apart from any direct satiety signaling by the dose, and lasting after the dose has ceased.

FIG DD4 illustrates another family or group of algorithms, labeled as "Algorithm B" in the figures. In this algorithm, the current is held substantially constant, while the frequency is ramped up and down in a dose. In this example, intensity (here current) is held constant for a half hour period, while frequency is ramped up and down for three ramps within a half hour long dose. In this example, current is held at 100 percent of MTC, while the frequency ramp is a linear ramp from 0 to 20 Hz for 5 minutes, then a ramp down from 20 Hz to 0 over 5 minutes, then two repeats of same. The inter-dose interval can be about 60 minutes, or the same times discussed with respect to Algorithm A, both for the doses and inter-dose intervals. The duty cycle can be 5 seconds on and 5 seconds off, in some embodiments.

FIG DD5 shows the doses delivered over a day, for the entire day and night. In some embodiments, stimulation is stopped during expected sleeping hours.

Algorithm B can be used to deliver variations of afferent signaling which may mimic the nutrient and mechanoreceptors which normally indicate the presence of food. The increasing and/or decreasing may aid in overcoming or preventing accommodation to the stimulation. Different populations of neurons may be effectively stimulated by different frequencies at the different times into each frequency ramp. In various embodiments, the dose/inter-dose times may be 10/20, 30/60, 80/160, and the like, with the times given in minutes. The frequency increasing portions may be about 5, 10, or 15 minutes long in some embodiments, as may the frequency decreasing portions in some embodiments. The frequency ramp portions can be configured such that the subsequent frequency ramps have substantially similar results as the first such ramps in the dose and/or compared to the same ramp in the next dose.

FIGS DD5 and DD6 illustrate another algorithm, labeled "Algorithm C." The dose and inter-dose times can be as previously described with respect to Algorithms B and C. Algorithm C can have a substantially constant stimulation intensity, shown here as 100 percent of MTC. Algorithm C can also have an increasing frequency ramp portion followed by a substantially constant frequency portion, followed by a decreasing frequency ramp portion. In this example, the frequency increases from about 0 to 20 Hz over about 15 minutes, then remains at about 20 Hz for 35 minutes, and then decreases back to about 0 Hz over about 10 minutes. In some embodiments, the frequency ramp up is about ¼ hour, the constant portion about ½ hour, and the ramp down about ¼ hour. In this example, the stimulation can either be run day and night or discontinued in expected sleeping times.

Other algorithms may also be used in some aspects of the present invention. Algorithm C can be varied having an 80 minute dose and a 160 minute inter-dose interval, with a 30 minute current ramp to maximum dose. The 30 minute ramp may provide a beneficial CV response at the dose onset, and has shown that in some tests. In another embodiment, Algorithm A is varied, to have a 30 min dose/60 minute inter-dose interval, with 24 hour application.

FIG XXX SHOWS Sites of FDG uptake corresponding to brown adipose tissue in adult humans. The black areas are those that are most frequently described; the gray areas are not always found, even in humans positive in the black areas. (A 3-dimensional representation of the distribution of brown adipose tissue FDG uptake in adult man is presently available at www.med.harvard.edu/JPNM/chetan/normals/brown_fat/case.html).

FIG YYY illustrates cold-induced brown adipose tissue activation in adult man. The same patient was investigated by fluorodeoxyglucose positron emission tomography (FDG PET) twice a few days apart.

(A): efforts had been made to keep the patient under warm conditions before injection and during the time from injection to imaging. The only uptake visible is that into the brain, heart, kidneys, and bladder.

(B): the patient had been examined under routine conditions, i.e., in comparatively cold conditions. Note that the characteristic symmetrical pattern of uptake into the supraclavicular, neck, paravertebral areas, etc., i.e., into brown adipose tissue, is now visible.

FIG MMM illustrates experimental results from an anesthetized rat. The top trace is the arterial pressure. The second from the top trace is the heart rate in BPM. The third from the top is the sympathetic nervous activity (SNA) as measured at the BAT, measured in micro volts.

The fourth trace from the top is the BAT temperature in degrees C., measured using a subcutaneous temperature probe. The fifth trace is the percent CO2, a measure of metabolic activity, however, this may have not been working properly.

The sixth trace from the top is the rate core temperature, measured in degrees C.

The seventh trace is the skin temperature.

The eight trace, at bottom, is an indication of whether the rat is being stimulated, at the GSN. The black blocks indicate stimulation of about 180 seconds in length. The stimulation parameters were all at 500 micro amp, and varied from in frequencies of 10 Hz 4 Hz, 20 Hz, and 10 Hz.

FIG MMM shows a rise in HR with each stim, and shows distinct SNA activity at the BAT, indicating that the GSN stimulation is coupled through the nervous system to the BAT. The BAT temperature can be seen to increase with each stimulation. Body core temperature is also seen to rise over the course of the experiment.

FIG NNN shows a similar result, using stimulation parameters of 800 micro amp, 4 Hz, and 0.4 ms pulse width. Each stimulation may be seen to increase BAT temperature. We believe the anesthesia or laboratory room temperature may have caused overall cooling over the course of the experiment.

FIG PPP illustrates another experiment. The arterial pressure is at top, the HR next, the BAT temperature next, with CO2 near bottom, and the stimulation indication blocks at bottom. The stimulation parameters used varying stimulation currents of 0.5 mA to 1 mA, (0.5 mA, 0.8 mA, and 1.0 mA), and stimulation frequencies of 4, 10, and 20 Hz. The pulse width was 0.4 msec. In the middle of the experiment, a 60 second on-60 second off stimulation pattern was used, and the BAT temperature may be seen to increase in direct response, as can the CO2 indication of increased metabolic activity.

The claims which follow are considered part of the originally filed specification by law.

We claim:

1. A method for placing an electrode for stimulating a sympathetic nerve for the purpose of inducing weight loss, the method comprising:

in a human patient having a back with an amount of brown adipose tissue located in the back and the human patient further having a sympathetic nervous system, determining the amount of brown adipose tissue (BAT) that the patient has located at each of the right side of the back of the patient and the left side of the back of the human;

selecting the greater amount side; and preferentially stimulating the sympathetic nervous system on the selected side.

2. The method of claim 1 and further comprising visualizing the BAT in the patient using a positron emission tomography (PET) scan.

3. The method of claim 1 in which the determining includes using a positron emission tomography (PET) scan while the patient is at a lower than 68 degrees F.

4. The method of claim 2 in which visualizing includes using the PET scan while the patient is at a lower than 68 degrees F.

5. The method of claim 1 and further comprising visualizing the BAT in the patient using an infra red image.

6. The method of claim 1, in which the determining includes determining the temperatures of BAT on the right and left side and selecting the side with the higher temperature.

7. The method of claim 6, in which the determining includes inserting a subcutaneous temperature probe in at least some of the BAT.

8. The method of claim 1, in which the electrode is placed on a splanchnic nerve.

9. The method of claim 1, in which the electrode is placed along the sympathetic chain.

* * * * *